United States Patent
Iwasaki et al.

(10) Patent No.: US 9,880,101 B2
(45) Date of Patent: Jan. 30, 2018

(54) FLOW RATE MEASUREMENT APPARATUS, ANTIGEN CONCENTRATION MEASUREMENT APPARATUS, FLOW CELL, FLOW RATE MEASUREMENT METHOD, AND ANTIGEN CONCENTRATION MEASUREMENT METHOD

(71) Applicant: Nippon Telegraph and Telephone Corporation, Tokyo (JP)

(72) Inventors: Yuzuru Iwasaki, Atsugi (JP); Tsutomu Horiuchi, Atsugi (JP); Michiko Seyama, Atsugi (JP); Toru Miura, Atsugi (JP); Tsuneyuki Haga, Atsugi (JP); Jun-ichi Takahashi, Atsugi (JP); Tsuyoshi Hayashi, Atsugi (JP)

(73) Assignee: Nippon Telegraph And Telephone Corporation, Tokyo (JP)

( * ) Notice: Subject to any disclaimer, the term of this patent is extended or adjusted under 35 U.S.C. 154(b) by 1336 days.

(21) Appl. No.: 13/857,514

(22) Filed: Apr. 5, 2013

(65) Prior Publication Data
US 2013/0224886 A1 Aug. 29, 2013

Related U.S. Application Data

(62) Division of application No. 12/811,400, filed as application No. PCT/JP2009/050433 on Jan. 15, 2009, now abandoned.

(30) Foreign Application Priority Data

Jan. 16, 2008 (JP) .................................. 2008-006651
Jul. 17, 2008 (JP) .................................. 2008-186043

(51) Int. Cl.
*G01N 21/75* (2006.01)
*G01F 1/704* (2006.01)
(Continued)

(52) U.S. Cl.
CPC ............. *G01N 21/75* (2013.01); *G01F 1/704* (2013.01); *G01F 1/712* (2013.01); *G01F 1/8468* (2013.01); *G01N 21/553* (2013.01); *G01P 5/18* (2013.01)

(58) Field of Classification Search
None
See application file for complete search history.

(56) References Cited

U.S. PATENT DOCUMENTS 4,982,342 A 1/1991 Moribe et al.
5,023,053 A 6/1991 Finlan
(Continued)

FOREIGN PATENT DOCUMENTS

JP 2001-194298 A 7/2001
JP 2002-214134 A 7/2002
(Continued)

OTHER PUBLICATIONS

Office Action, U.S. Appl. No. 12/811,400, dated Jan. 27, 2012.
(Continued)

*Primary Examiner* — Melanie Y Brown
*Assistant Examiner* — Richard Moerschell
(74) *Attorney, Agent, or Firm* — Harness, Dickey & Pierce, P.L.C.

(57) ABSTRACT

A flow rate measurement apparatus includes a light oscillator; a thin metallic film which causes surface plasmon resonance by light output from the light oscillator; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and (Continued)

the reference areas being alternately arranged at a location along the focal line location on the thin metallic film; a light receiver which receives reflected light, at the focal line location, of the output light by surface plasmon resonance occurring at the focal line location, at each of the plurality of incident light angles; an SPR angle calculator which obtains a temporal change of an SPR angle in each of the antibody fixed areas and the reference areas in the measurement part; and a flow rate operation unit which calculates the flow rate of the sample flowing in the flow cell based on the temporal change of the SPR angle obtained by the SPR angle calculator.

20 Claims, 14 Drawing Sheets

(51) Int. Cl.
<table>
<tr><td>G01F 1/712</td><td>(2006.01)</td></tr>
<tr><td>G01F 1/84</td><td>(2006.01)</td></tr>
<tr><td>G01N 21/552</td><td>(2014.01)</td></tr>
<tr><td>G01P 5/18</td><td>(2006.01)</td></tr>
</table>

(56) References Cited

U.S. PATENT DOCUMENTS

| | | |
|---|---|---|
| 5,981,262 A | 11/1999 | Brugge et al. |
| 7,530,692 B2 | 5/2009 | Yamaguchi et al. |
| 2003/0067612 A1 | 4/2003 | Ivarsson |
| 2003/0124623 A1 | 7/2003 | Yager et al. |
| 2006/0087656 A1* | 4/2006 | Barford ............... G01N 21/553 356/445 |
| 2007/0065954 A1 | 3/2007 | Taya et al. |
| 2007/0210268 A1 | 9/2007 | Yamamichi et al. |
| 2007/0222998 A1 | 9/2007 | Sasaki et al. |

FOREIGN PATENT DOCUMENTS

| | | |
|---|---|---|
| JP | 3356213 B2 | 7/2002 |
| JP | 2003-232725 A | 8/2003 |
| JP | 2005-512045 A | 4/2005 |
| JP | 2006-266906 A | 10/2006 |
| JP | 2007-192806 A | 8/2007 |
| JP | 2007-240501 A | 9/2007 |
| JP | 2007-248253 A | 9/2007 |
| WO | 90/05295 A1 | 5/1990 |
| WO | 2007/072986 A1 | 6/2007 |
| WO | 2007/145180 A1 | 12/2007 |

OTHER PUBLICATIONS

Office Action, U.S. Appl. No. 12/811,400, dated Jun. 27, 2012.
Milan Mrksich et al., "Surface Plasmon Resonance Permits in Situ Measurement of Protein Adsorption on Self-Assembled Monolayers of Alkanethiolates on Gold", American Chemical Society, Langmuir, 1995, 11, pp. 4383-4385.
Yuzuru Iwasaki et al., "Imaging of flow pattern in micro flow channel using surface plasmon resonance", Measurement Science and Technology, 17, 2006, pp. 3184-3188.
International Search Report, Application No. PCT/JP2009/050433, dated Apr. 21, 2009.

* cited by examiner

FLOW RATE MEASUREMENT APPARATUS, ANTIGEN CONCENTRATION MEASUREMENT APPARATUS, FLOW CELL, FLOW RATE MEASUREMENT METHOD, AND ANTIGEN CONCENTRATION MEASUREMENT METHOD

TECHNICAL FIELD

The present invention relates to a flow rate measurement apparatus, an antigen concentration measurement apparatus, a flow cell, a flow rate measurement method, and an antigen concentration measurement method.

The present application claims priority on Japanese Patent Applications No. 2008-006651 filed on Jan. 16, 2008 and No. 2008-186043 filed on Jul. 17, 2008, the entire contents of which are incorporated herein by reference.

BACKGROUND ART

A method used to detect an antigen concentration includes forming an antibody fixed film having an antibody attached to a thin metallic film exposed to a flow path portion of a flow cell, flowing liquid containing an antigen in the flow cell, detecting the antigen attached to the antibody, i.e., a change of a refractive index of the antibody fixed film due to an antigen-antibody complex using a surface plasmon resonance sensor, and detecting a concentration of the antigen from a rate of change of the refractive index (see, for example, Non-Patent Document 1).

Accordingly, since the rate of change of the refractive index increases with the antigen concentration, the antigen concentration is measured from the rate of change.

A surface plasmon resonance (hereinafter, referred to as SPR) measurement apparatus has recently been studied as a bio sensor using light (see, for example, Patent Documents 1 and 2). In the antigen concentration measurement apparatus, a device in which a measured substance, such as an antibody, is fixed on a thin metallic film, such as gold or silver, is used as a measurement flow cell. Light is emitted from a surface opposing the antibody of the flow cell, and an incident angle at which a resonance between an evanescence wave and a surface plasmon wave occurs is measured.

FIG. 18 is a schematic block diagram showing a configuration of a conventional antigen concentration measurement apparatus. The antigen concentration measurement apparatus has a prism 1001, a light source 1002, a polarizer 1003, a focusing lens 1004, and a CCD camera 1005.

When light radiated from the light source 1002 for monochromatic light passes through the polarizer 1003, only P-polarized light passes. This P-polarized light is focused by the focusing lens 1004 and emitted to the hemispherical prism 1001. A flow cell 1000 is disposed on an upper surface of the prism 1001, and the P-polarized light is emitted from a surface opposing the surface to which a measured substance, such as an antibody, is fixed. Thus, the P-polarized light is emitted to the flow cell 1000 at an incident angle θ via the prism 1001, such that a change of intensity of reflected light from the flow cell 1000 is detected by the CCD camera 1005.

The light radiated from the light source 1002 is converted into an evanescent wave at an interface between the prism 1001 and the thin metallic film of the flow cell 1000. Meanwhile, a surface plasmon wave is generated on a surface of the thin metallic film. At an incident angle θ at which a wave number of the evanescent wave is coincident with that of the surface plasmon wave, the evanescent wave is used to excite the surface plasmon wave and a light amount measured from the reflected light is reduced.

In this case, if the intensity of the reflected light is measured by the CCD camera 1005, degradation of the reflectivity is observed at an incident angle at which the resonance between the evanescence wave and the surface plasmon wave occurs, as shown in FIG. 19. On an incident angle-reflectivity curve indicating a relationship between the incident angle and the reflectivity, this is shown as a valley with low reflectivity around the incident angle at which the resonance between the evanescence wave and the surface plasmon wave occurs.

Since the angle at which the resonance between the evanescence wave and the surface plasmon wave occurs depends on a refractive index of the measured substance contiguous to the thin metallic film of the flow cell 1000, when the measured substance such as an antibody is fixed on the thin metallic film, the refractive index of the antibody is changed due to coupling with the antigen, and the angle at which the valley is shown undergoes a slight change, which can be measured to determine an amount of the measured substance.

Patent Document 1: Japanese Patent Application, First Publication No. 2001-194298
Patent Document 2: Japanese Patent No. 3356213
Non-Patent Document 1: Milan Mrksich, George B. Sigal, and George M. Whitesides, "Surface Plasmon Resonance Permits in Situ Measurement of Protein Adsorption on Self-Assembled Monolayers of Alkanethiolates on Gold," American Chemical Society, Langmuir, 1995, 11, 4383-4385

DISCLOSURE OF INVENTION

Problem to be Solved by the Invention

However, in a conventional measurement such as in Non-Patent Document 1, when different antibodies are fixed in a flow direction of a flow cell and timings at which a sample flowing in the flow cell reaches the each antibodies are unknown, accurate antigen concentration measurement cannot be performed due to the antigen concentration measurement being detected by a rate of change of the SPR angle.

Further, when a CCD camera is used to detect intensity of reflected light from incident light in order to detect the rate of change of the SPR angle, noise overlaps according to a frame rate of the CCD camera, which may make it difficult to identify a beginning of a change of an antigen-antibody reaction (a change point of the SPR angle).

Accordingly, it is necessary to accurately measure the flow rate of the sample in order to accurately recognize timings at which the sample reaches each antibodies. However, since a portion measured at the SPR angle is a portion adjacent to a flow path wall within 1 μm or less from the metal film and a flow rate distribution in the flow path is changed with the viscosity of the sample, and so on, it is impossible to determine an effective flow rate affecting the SPR angle measurement using only a liquid transfer mechanism, such as a pump, and it is necessary to measure the flow rate in the flow path for each SPR angle measurement.

The present invention has been achieved in view of the above circumstances, and it is an object of the present invention to provide a flow rate measurement apparatus, an antigen concentration measurement apparatus, a flow cell, a flow rate measurement method, and an antigen concentration measurement method that are capable of accurately measuring the flow rate of the sample in the flow cell and detecting an antibody area that a sample reaches in an area to which a plurality of serially arranged antibodies are fixed.

Means for Solving the Problem (1) A flow rate measurement apparatus of the present invention which measures a flow rate of a sample flowing in a long flow cell, different antibodies being arranged in a sample flow direction in the flow cell, includes: a light oscillator; a thin metallic film which causes surface plasmon resonance by light output from the light oscillator; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and the reference areas being alternately arranged at a location along the focal line location on the thin metallic film; a light receiver which receives reflected light, at the focal line location, of the output light by surface plasmon resonance occurring at the focal line location, at each of the plurality of incident light angles; an SPR angle calculator which obtains a temporal change of an SPR angle in each of the antibody fixed areas and the reference areas in the measurement part; and a flow rate operation unit which calculates the flow rate of the sample flowing in the flow cell based on the temporal change of the SPR angle obtained by the SPR angle calculator.

(2) Preferably, the flow rate operation unit of the flow rate measurement apparatus of the present invention includes a waveform shifter which shifts one of curves (referred to as adsorption curves) indicating the temporal change of the SPR angles at two points in either the antibody fixed area or the reference area with respect to the other in a time direction; a time difference detector which measures a shift time at which a difference between the SPR angles at the two points is smallest; and a flow rate calculator which calculates the flow rate of the sample in the flow cell by dividing a location between the two points by the shift time.

(3) The flow rate measurement apparatus of the present invention may further include a waveform differentiation operation unit which performs time differentiation on the adsorption curves for the two each points to obtain differential curves, wherein the waveform shifter may shift one of the differential curves for the two each points with respect to the other in a time direction, and the time difference detector may measure a shift time at which a difference between the SPR angles in the differential curves for the two each points is smallest.

(4) The flow rate measurement apparatus of the present invention may further include a waveform differentiation operation unit which performs time differentiation on differential data of the SPR angles, wherein the waveform shifter may shift one of the adsorption curves for the two each points with respect to each other in a time direction. Each time the waveform shifter shifts the adsorption curve, the waveform differentiation operation unit may perform the time differentiation on differential data of the adsorption curves for the two each points, and the time difference detector may measure a shift time at which the time-differentiated differential data of SPR angles in the adsorption curves for the two each points is smallest.

(5) The flow rate operation unit of the flow rate measurement apparatus of the present invention may calculate the flow rate of the sample flowing in the flow cell using Hough conversion.

(6) The antibody, and a sample detection substance having a refractive index varying by reacting with a substance other than a substance expected to react with the antibody among substances contained in the sample may be fixed on the thin metallic film. The flow rate measurement apparatus of the present invention may further include a reaction-result derivation unit which obtains a resonant angle that is an incident angle at which reflectivity is smallest based on a correlation between the incident angle of the incident light and reflectivity of the reflected light in the antibody, and obtains a reaction amount between the antibody and the sample detection substance from the resonant angle; a refractive-index derivation unit which obtains a resonant angle based on a correlation between the incident angle and reflectivity in the sample detection substance, and obtains refractive indices of the sample detection substance and the substance contained in the reacting sample from the resonant angle; and a reaction-result correction unit which obtains an amount of error for the flow rate of the sample from a rate of change of the refractive index obtained by the refractive-index derivation unit and obtains a correction amount for the reaction amount obtained by the reaction-result derivation unit from an amount of error of the flow rate to correct the reaction amount based on the correction amount.

(7) The flow rate measurement apparatus of the present invention may further include a measurement-initiation-signal output unit which outputs a measurement initiation signal when the resonant angle is obtained from the correlation between then incident angle and the reflectivity obtained by the image processor and the sample beginning to flow on the flow cell is detected from a change of the resonant angle; and an image acquisition period controller which iteratively outputs an image acquisition timing signal to instruct the light receiver to acquire an image, making the period of the image acquisition timing signal shorter than the normal period between an output time of the measurement initiation signal and a predetermined time, and returning the period of the image acquisition timing signal to the normal period after the predetermined time lapses.

(8) The flow rate measurement apparatus of the present invention may further include a storage unit in which the ideal value of the rate of change of the refractive index, a relationship between the amount of error of the rate of change and the amount of error for the flow rate of the sample, and a relationship between the amount of error of the flow rate and the correction amount are registered in advance, wherein the reaction-result correction unit obtains an amount of error between the rate of change of the refractive index obtained by the refractive-index derivation unit and the ideal value of the rate of change registered in the storage unit, acquires the amount of error of the flow rate corresponding to the amount of error of the rate of change from the storage unit, and acquires the correction amount corresponding to the amount of error of the flow rate from the storage unit.

(9) An antigen concentration measurement apparatus of the present invention which measures a concentration of antigen contained in a sample, different antibodies being arranged in a sample flow direction in a long flow cell, includes: a light oscillator; a thin metallic film which causes surface plasmon resonance by light output from the light oscillator, the antibody and a sample detection substance having a refractive index varying by reacting with a substance other than antigen expected to react with the antibody among substances contained in the sample being fixed on the thin metallic film; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and the reference areas being alternately arranged at a location along the focal line location on the thin metallic film; a light receiver which receives reflected light, at the focal line location, of the output light by surface plasmon resonance occurring at the focal line location, at each of the plurality of incident light angles; an SPR angle calculator which obtains a temporal change of an SPR angle in each of the antibody fixed areas and the reference areas in the measurement part; a flow rate operation unit which calculates a flow rate of the sample flowing in the flow cell based on the temporal change of the SPR angle obtained by the SPR angle calculator; a reaction-result derivation unit which obtains a resonant angle that is an incident angle at which reflectivity is smallest based on a correlation between the incident angle of the incident light and reflectivity of the reflected light in the antibody, and obtains a reaction amount between the antibody and the sample detection substance from the resonant angle; a refractive-index derivation unit which obtains a resonant angle based on a correlation between the incident angle and reflectivity in the sample detection substance, and obtains refractive indices of the sample detection substance and the substance contained in the reacting sample from the resonant angle; a reaction-result correction unit which obtains an amount of error for the flow rate of the sample from a rate of change of the refractive index obtained by the refractive-index derivation unit and obtains a correction amount for the reaction amount obtained by the reaction-result derivation unit from an amount of error of the flow rate to correct the reaction amount based on the correction amount; and an antigen concentration calculation unit which calculates a concentration of the antigen contained in the sample based on the correction result from the reaction result correction unit.

(10) The flow cell of the present invention for surface plasmon resonance measurement has a thin metallic film on which an antibody is fixed in a portion thereof. The antibody and a sample detection substance having a refractive index varying by reacting with a substance other than an antigen expected to react with the antibody among substances contained in the sample flowing in the flow cell are fixed on the thin metallic film.

(11) In the flow rate measurement method of the present invention, a flow rate of a sample flowing in a long flow cell is measured using a flow rate measurement apparatus comprising: a light oscillator, a thin metallic film which causes surface plasmon resonance by light output from the light oscillator; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and the reference areas being alternately arranged in the flow cell and the flow cell being formed at a location along the focal line location on the thin metallic film; and a light receiver which receives reflected light, at the focal line location, of the output light by surface plasmon resonance occurring at the focal line location, at each of the plurality of incident light angles. The method includes: an SPR angle calculation process of obtaining a temporal change of an SPR angle in each of the antibody fixed areas and the reference areas in the measurement part; and a flow rate operation process of calculating the flow rate of the sample flowing in the flow cell based on the temporal change of the SPR angle obtained by the SPR angle calculator.

(12) The antigen concentration measurement method of the present invention is a flow rate measurement method of measuring a flow rate of a sample flowing in a long flow cell using a flow rate measurement apparatus comprising: a light oscillator; a thin metallic film which causes surface plasmon resonance by light output from the light oscillator, the antibody and a sample detection substance having a refractive index varying by reacting with a substance other than antigen expected to react with the antibody among substances contained in the sample being fixed on the thin metallic film; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and the reference areas being alternately arranged in the flow cell and the flow cell being formed at a location along the focal line location on the thin metallic film; and a light receiver which receives reflected light, at the focal line location, of the output light by surface plasmon resonance occurring at the focal line location, at each of the plurality of incident light angles. The method includes: an SPR angle calculation process of obtaining a temporal change of an SPR angle in each of the antibody fixed areas and the reference areas in the measurement part; a flow rate operation process of calculating a flow rate of the sample flowing in the flow cell based on the temporal change of the SPR angle obtained in the SPR angle calculation process; a reaction-result derivation process of obtaining a resonant angle that is an incident angle at which reflectivity is smallest based on a correlation between the incident angle of the incident light and reflectivity of the reflected light in the antibody, and obtaining a reaction amount between the antibody and the sample detection substance from the resonant angle; a refractive-index derivation process of obtaining a resonant angle based on a correlation between the incident angle and reflectivity in the sample detection substance, and obtaining refractive indices of the sample detection substance and the substance contained in the reacting sample from the resonant angle; a reaction-result correction process of obtaining an amount of error for the flow rate of the sample from a rate of change of the refractive index obtained in the refractive-index derivation process and obtaining a correction amount for the reaction amount obtained in the reaction-result derivation process from an amount of error of the flow rate to correct the reaction amount based on the correction amount; and an antigen concentration calculation process of calculating a concentration of the antigen contained in the sample based on the correction result in the reaction result correction process.

Effect of the Invention

In the flow rate measurement apparatus, the antigen concentration measurement apparatus, the flow cell, the flow rate measurement method, and the antigen concentration measurement method of the present invention, the flow rate of the sample in the flow cell can be accurately measured, and an antibody area that the sample reaches can be detected in the area to which a plurality of serially arranged antibodies are fixed.

REFERENCE SYMBOLS

1 . . . prism, 2 . . . light source, 3 . . . polarizer, 4 . . . focusing lens, 5 . . . CCD camera, 6 . . . data processing device, 7 . . . database, 8 . . . pump, 9 . . . flow path, 10 . . . sample cell, 11 . . . data input unit, 12 . . . data storage unit, 13 . . . SPR angle calculator, 14 . . . interpolation operation unit, 15 . . . waveform shifter, 16 . . . waveform differentiation operation unit, 17 . . . waveform subtractor, 18 . . . standard-deviation operation unit, 19 . . . time difference detector, 20 . . . flow rate calculator, 21a and 21b . . . flow rate operation unit, 22 . . . antigen concentration calculator, 23 . . . waveform differentiation and square unit, 24 . . . straight line detector, 25 . . . flow rate detector, 60 . . . controller, 61 . . . storage unit, 62 . . . input unit, 63 . . . display unit, 64 . . . image acquisition period controller, 65 . . . image processor, 66 . . . measurement-initiation-signal output unit, 67 . . . reaction-result derivation unit, 68 . . . refractive-index derivation unit, 69 . . . reaction-result correction unit, 100 . . . LED, 101, 108, and 110 . . . lens, 102 and 109 . . . polarizer, 103 . . . cylindrical lens, 104 . . . prism, 105 . . . thin metallic film, 106 . . . antibody fixed film, 107 . . . focal line, 111 . . . CCD (charge coupled device), 112 . . . data processing device, 113a and 113b . . . controller, 300a and 300b . . . antigen concentration detecting apparatus

BEST MODE FOR CARRYING OUT THE INVENTION

Hereinafter, an antigen concentration measurement apparatus according to each embodiments of the present invention will be described with reference to the accompanying drawings. First, a first embodiment of the present invention will be described.

First Embodiment

Figure 1:
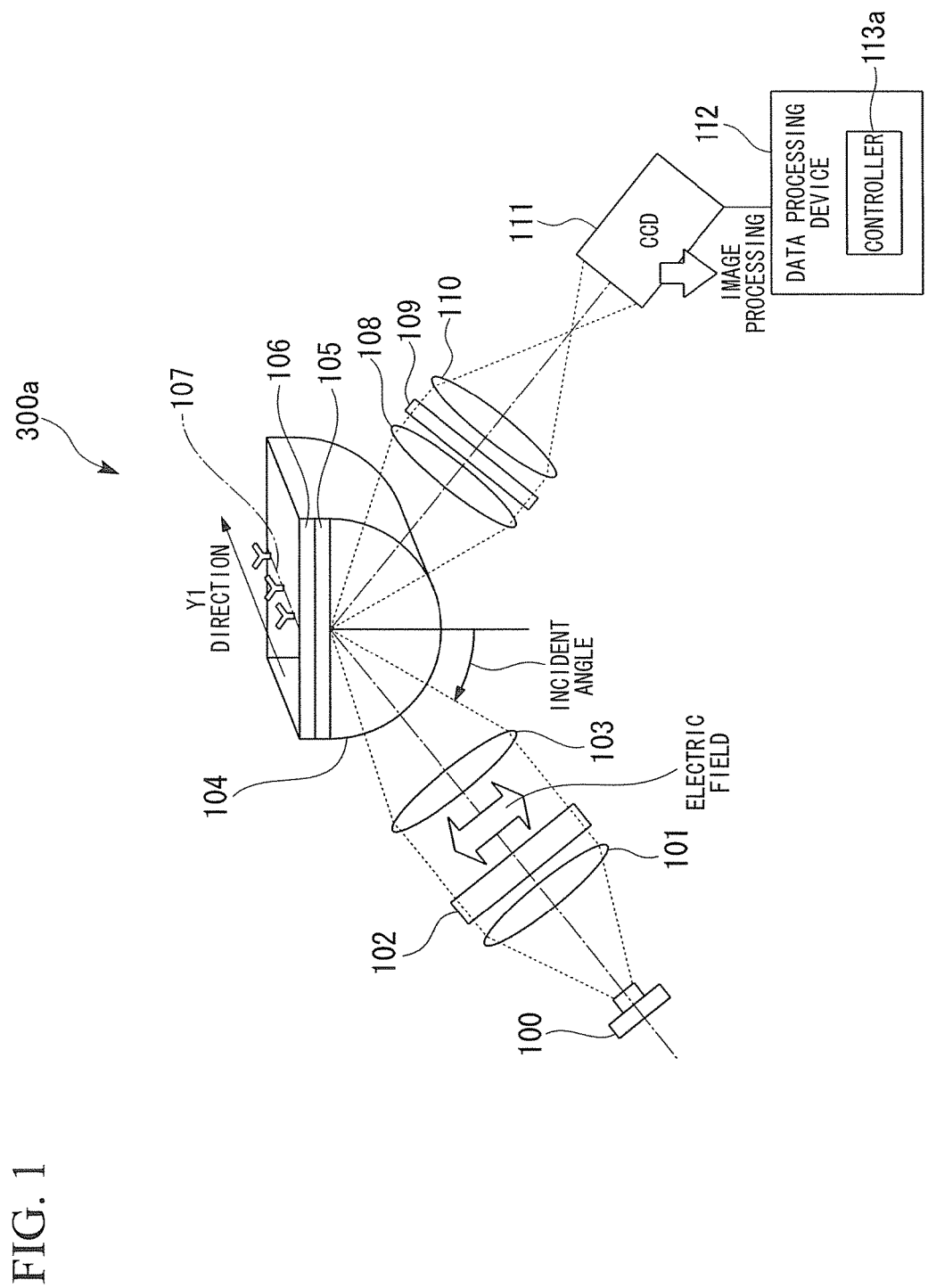
FIG. 1 is a block diagram showing an example of a configuration of an optical measurement part which measures an SPR angle in an antigen concentration detection apparatus 300a according to a first embodiment of the present invention.

FIG. 1 is a block diagram showing an example of a configuration of an optical measurement part of an antigen concentration measurement apparatus 300a according to a first embodiment of the present invention.

In a configuration of the antigen concentration measurement apparatus 300a (referred to also as a flow rate measurement apparatus), light from a light emitting diode (LED) 100 serving as a light source (referred to also as a light oscillator) is emitted as a light beam to a lens 101, and only P-polarized light from a polarizer 102 is focused by a cylindrical lens 103 and emitted to a prism 104 having a high refractive index. The light source may be a semiconductor laser or the like, as well as the LED 100.

The prism 104 is formed so that a focal line 107 of the light focused by the cylindrical lens 103 reaches a surface opposing a surface to which the light is emitted in parallel with an axial direction of a cylinder.

An antibody corresponding to an antigen of which the concentration is to be measured is fixed on a thin metallic film 105 (e.g., a thin golden film) for surface plasmon resonance, thereby forming an antibody fixed film 106 on the opposite surface. This thin metallic film 105 is formed (fixed) on the prism 104, which is an optically transparent medium.

Light emitted to the prism 104 is reflected by liquid flowing in the thin metallic film 105, the antibody fixed film 106, and the flow path, at a location of the focal line 107. The reflected light is collimated by a lens 108 and only P-polarized light is emitted to a lens 110 due to a polarizer 109. The lens 110 radiates the incident light to a surface of a CCD 111 (CCD) serving as a light receiving element. These constitute a focusing unit, on the thin metallic film 105, for converting the light output from the LED 100 into the incident light having a plurality of incident angles and focusing the incident light at the location of the straight focal line 107. Pixel data photographed by the CCD 111 is output to the data processing device 112. The data processing device 112 has a controller 113a.

Figure 2:
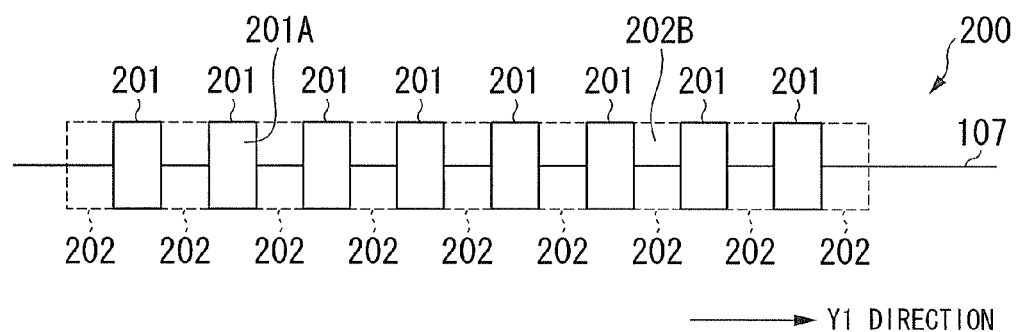
FIG. 2 is a conceptual diagram showing a configuration of a flow cell in which antibody fixed areas 201 and reference areas 202 are alternately disposed in parallel with a focal line 107 along the focal line 107 in an antibody fixed film of FIG. 1.

In the thin metallic film 105, a sample area 200 consisting of antibody fixed areas 201 to which the antibody is fixed and reference areas 202 to which the antibody is not fixed is disposed as a measurement area (referred to also as a measurement part) on the focal line 107, with the antibody fixed areas 201 and the reference areas 202 arranged alternately at previously set periods with respect to a direction of the focal line 107 (i.e., a Y1 direction), as shown in FIG. 2. Although not shown, a flow path of a flow cell (referred to also as a micro flow cell or sample cell) is formed to cover an arrangement of the antibody fixed areas 201 and the reference areas 202 in a direction parallel to the focal line 107 (i.e., an arrangement direction in which the antibody fixed areas 201 and the reference areas 202 are alternately disposed) and to allow a sample to sequentially reach the antibody fixed areas 201 and the reference areas 202.

Figure 3:
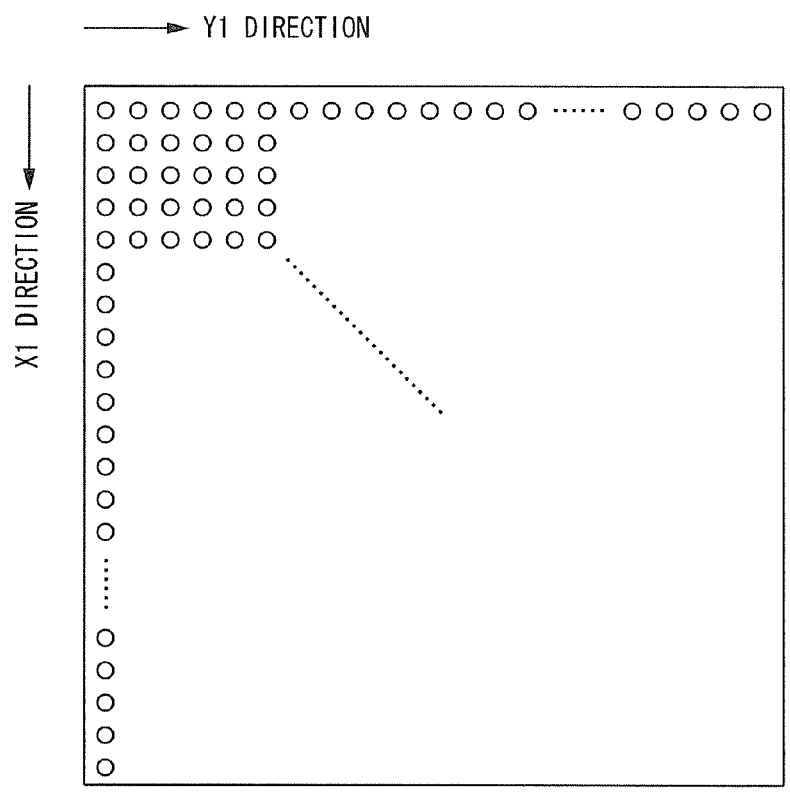
FIG. 3 is a conceptual diagram showing a configuration of a distribution of reflected light from a thin metallic film 105 input to two-dimensionally disposed light receiving elements of a CCD 111 in FIG. 1.

Accordingly, on the CCD 111 surface, reflected light from the surface of the focal line 107 is input to light receiving elements arranged in a lattice shape in units of pixels, which correspond to locations in the Y1 direction on the surface of the focal line 107, as shown in FIG. 3 that shows an upper surface of the CCD 111.

Further, the light reflected from the focal line 107, corresponding to the incident angle, is input in an X1 direction. Accordingly, intensities of the reflected lights, at the each incident angles at each focal line locations, of the light irradiated to the focal line 107 in parallel with the sample area 200 can be detected together.

In the above-described configuration, when an antigen reacts with the antibody fixed to each antibody fixed area 201 and is coupled to the antibody, a refractive index of the antibody fixed film 106 is changed and reflectivity at an incident angle corresponding to the refractive index is changed. Thus, it is possible to measure the change of the refractive index of the antibody fixed film 106 by monitoring the incident angle (SPR angle) at which the reflectivity decreases according to time as the refractive index increases when the antigen is attached to the antibody.

That is, the incident angle causing surface plasmon resonance is shifted as the antigen is adsorbed to the antibody. However, since the incident angle is shifted even by simple adsorption in addition to the antigen-antibody reaction, it is necessary to detect the SPR shift caused by only the antigen-antibody reaction for high precision for measurement of the antigen concentration by subtracting the shift of the SPR angle of the reference area 202 to which the antibody is not fixed, as the reference value, from the SPR shift of the antibody fixed area 201 to which the antibody is fixed.

Next, the SPR angle will be described.

The light emitted from the LED 100 to the prism 104 causes an evanescent wave to be generated at an interface between the prism 104 and the thin metallic film 105. A wave number $k_{ev}$ of the evanescent wave is defined by Equation (1):

$$k_{ev}=k_p n_p \sin \theta \quad (1)$$

where $k_p$ denotes a wave number of the incident light, $n_p$ denotes a refractive index of the prism 104, and $\theta$ denotes the incident angle.

Meanwhile, a surface plasmon wave is generated on a surface of the thin metallic film 105. A wave number $k_{sp}$ of the surface plasmon wave is defined by Equation (2):

$$k_{sp}=(c/\omega)\{\epsilon n2/(\epsilon+n2)\}^{1/2} \quad (2)$$

where c denotes light velocity, $\omega$ denotes an angular frequency, $\epsilon$ denotes permittivity of the thin metallic film 105, and n denotes a refractive index of the measured object.

At an incident angle $\theta$ at which the wave number $k_{ev}$ of the evanescent wave matches the wave number $k_{sp}$ of the surface plasmon wave, energy of the evanescent wave is used to excite the surface plasmon and intensity of the reflected light is reduced. Accordingly, an incident angle-reflection intensity curve having a minimum value at a predetermined angle $\theta 0$ (SPR angle) is obtained by changing the incident angle $\theta$. That is, the reflected light including absorption due to a surface plasmon resonance phenomenon is reflected from the interface between the thin metallic film 105 and the prism 104.

This SPR phenomenon depends on a refractive index n of an antigen-antibody complex of a sample of the measured object contiguous to the thin metallic film 105. Accordingly, a refractive index change, and so on due to a concentration change of the antigen contained in the sample can be measured from an angle $\theta 0$ corresponding to the minimum value.

Figure 4:
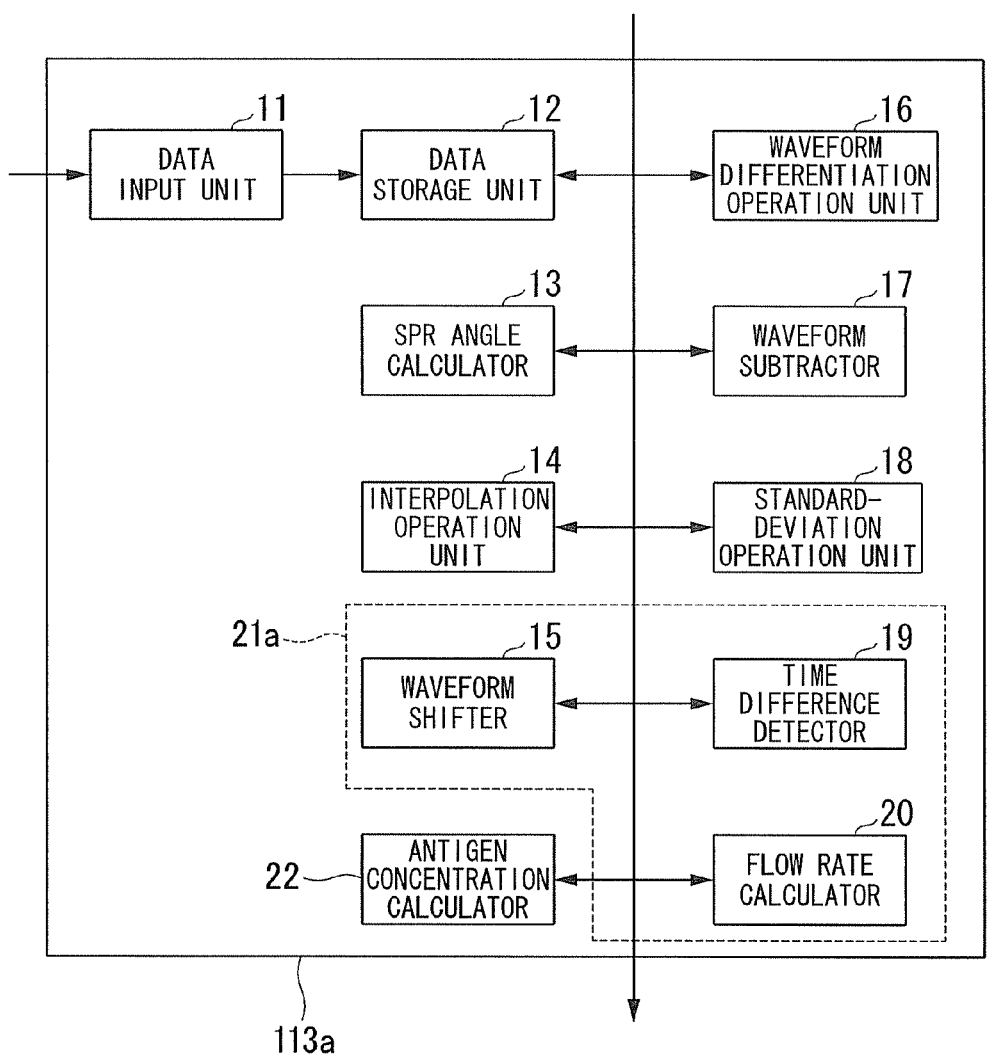
FIG. 4 is a block diagram showing a configuration which detects a flow rate of a sample in a flow cell in an antigen concentration detecting apparatus 300a of the present embodiment.

Next, a controller which calculates a flow rate in the antigen concentration measurement apparatus 300a according to the present embodiment will be described with reference to the accompanying drawings. FIG. 4 is a block diagram showing an example of a configuration of a controller 113a which performs flow rate calculation according to the present embodiment.

In FIG. 4, the controller 113a has a data input unit 11, a data storage unit 12, an SPR angle calculator 13, an interpolation operation unit 14, a waveform shifter 15, a waveform differentiation operation unit 16, a waveform subtractor 17, a standard-deviation operation unit 18, a time difference detector 19, and a flow rate calculator 20.

Pixel data of each light receiving element, i.e., pixel data indicating reflection intensity of the light receiving element corresponding to each location in the arrangement direction of the antibody fixed areas 201 and an incident angle in a previously set incident angle range in each location is input, as arrangement frame image data, from a CCD 111 of the SPR sensor in FIG. 1.

Figure 5:
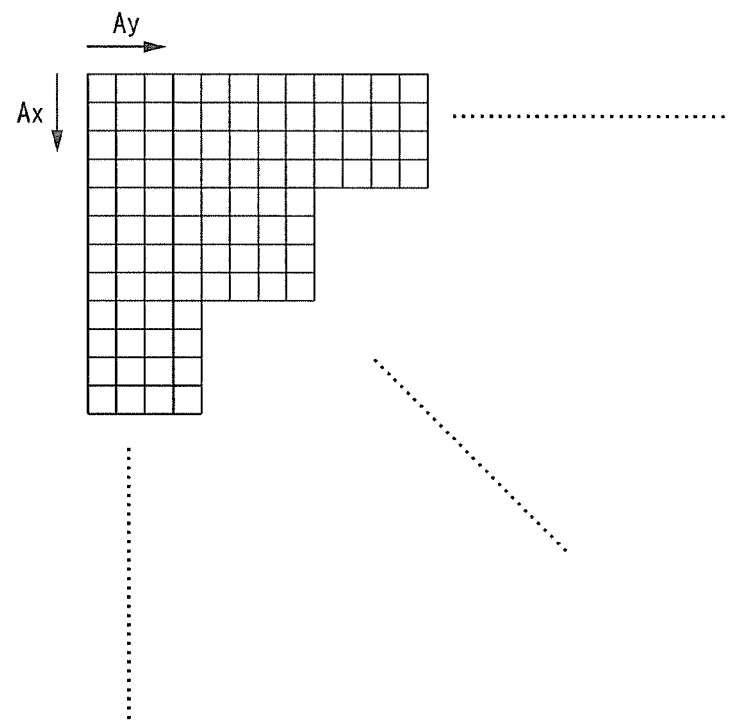
FIG. 5 is a conceptual diagram showing a configuration of a storage area in a data storage unit 12 for the gradient of the reflection intensity of light received by a light receiving element, at an address corresponding to a location in a Y1 direction and a location in an X1 direction of each light receiving element in a CCD 111.

The data input unit 11 converts a voltage value that is the pixel data of each light receiving element input from the CCD 111 into a corresponding gradient, and stores gradient data indicating reflection intensity of light received by the light receiving element corresponding to each address as arrangement frame image data organized as shown in FIG. 5 to correspond to an address set by an address Ay corresponding to a location of each light receiving element in the Y1 direction (an arrangement of the antibody fixed areas 201 and the reference areas 202) and an address Ax corresponding to a location in the X1 direction (a location corresponding to the incident angle), in the data storage unit 12 every sampling time.

Here, where the reflection intensity is high, the gradient is high and where the reflection intensity is low, the gradient is low. For example, the data input unit 11 standardizes maximum reflection intensity obtained through experiment, as a maximum gradient, and converts the input voltage value into a gradient.

The SPR angle calculator 13 obtains SPR angles at each previously set location of the antibody fixed area 201, for example, in the antibody fixed area 201 of FIG. 2 (e.g., the antibody fixed area 201A of FIG. 2) and the reference area 202 (e.g., the reference area 202B), in a sampling time unit, from the data stored in the data storage unit 12, and stores the SPR angles to correspond to the sampling time, as SPR measurement data DA and SPR measurement data DB, in the data storage unit 12.

Figure 6:
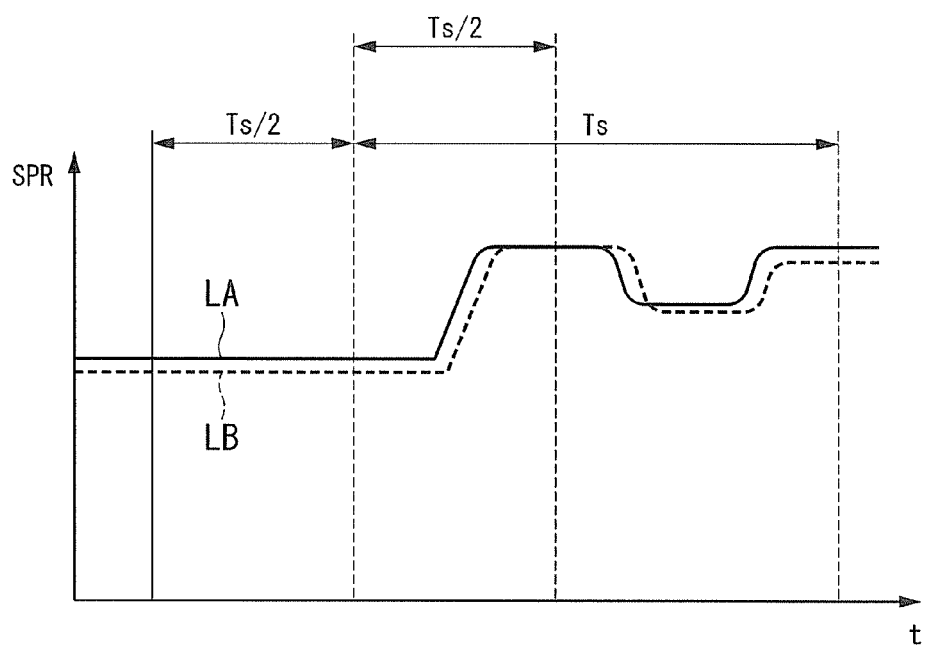
FIG. 6 is a graph showing a temporal change of an SPR angle in an antibody fixed area 201 and a reference area 202.

Further, the controller displays the SPR measurement data A and B as adsorption curves LA and LB on the display unit, as shown in FIG. 6.

The waveform differentiation operation unit 16 performs numerical differentiation by time (hereinafter, time differentiation) on the adsorption curve LA and the adsorption curve LB to produce a differential curve DA and a differential curve DB.

The interpolation operation unit 14 performs interpolation, e.g., linear interpolation on the differential curve DB in units of time D1. Here, when the sampling period is Ts and the interpolation is performed with a resolution of 1/n, the time D1 is determined by:

$$D1 = Ts/n$$

The waveform shifter 15 shifts the differential curve DB by a previously set time D2 and then shifts a 2×D2 time range by the time D1. For example, in the present embodiment, the set time D2 is −(½)Ts, by which the differential curve DB is shifted in parallel.

Further, the waveform shifter 15 adds a time D1 to the set time D2 to obtain a new set time D2 and iteratively shifts the differential curve DB in a positive direction from an original location while increasing the set time D2 by the time D1 until the set time D2 becomes (½)Ts, i.e., until a range of the shift time becomes Ts.

At each time, the waveform subtractor 17 subtracts the SPR angle of the differential curve DB from the SPR angle of the differential curve DA each corresponding time, to obtain SPR differential data of each time, for each value of the set time D2.

The standard-deviation operation unit 18 obtains a standard deviation of the SPR differential data of each time within the measurement range (Ts) of the adsorption curve LA, for each value of the set time D2.

The time difference detector 19 detects a value of the set time D2 having the smallest standard deviation of the SPR differential data of each time. This set time D2 is a time difference between times when the sample reaches the antibody fixed area 201 and the reference area 202.

The flow rate calculator 20 obtains a flow rate by dividing a distance between the antibody fixed area 201 and the reference area 202 by the time difference.

Further, the waveform shifter 15, the time difference detector 19, and the flow rate calculator 20 are also collectively termed as a flow rate operation unit 21a. The flow rate operation unit 21a calculates the flow rate of the sample flowing in the flow cell based on the temporal change of the SPR angle obtained by the SPR angle calculator 13, as described above.

Timings at which the sample reaches the antibody fixed areas 201 and the reference area 202s disposed in series in parallel with a flow direction of the sample in the flow cell can be detected from the flow rate of the sample flowing in the flow cell. The antigen concentration measurement part 22 calculates the antigen concentration from the rate of change of the SPR angle. That is, the antigen concentration measurement part 22 estimates an antigen concentration from a temporal change of an SPR angle in each antibody fixed area 201 by performing a comparison with the result of the temporal change of the SPR angle in a sample having predetermined antigen concentration.

The above-described method of detecting the flow rate of the sample in the present embodiment can measure a flow rate in a local area (an interfacial area between the thin metallic film surface and the sample) in which a distance from the thin metallic film surface detected by the SPR angle measurement is 400 nm or less, which is an effective flow rate affecting the SPR angle measurement, unlike the case where a volume flow rate is set in a pump or the like. Even when there is a flow rate distribution in the flow path, an adjacent combination is selected from the antibody fixed areas 201 and the reference areas 202 of FIG. 2 and a plurality of antibody fixed areas and reference areas are provided, such that the flow rate of the sample around the antibody fixed area 201 and the reference area 202 in each set can be measured.

Since an adsorption component (having no relation with the antigen-antibody reaction) and a random noise component are included in the adsorption curves LA and LB, and a change of the SPR angle due to the adsorption component is a slow component (drift component), weight effect from drift and noise component can be reduced by a differentiation operation, therefore flow rate estimation precision can be improved.

Further, although in the present embodiment, the differential curve DA is fixed and the differential curve DB is shifted in parallel, conversely, the differential curve DB may be fixed and the differential curve DA may be shifted to obtain the flow rate similarly.

Meanwhile, the inventor has obtained a flow rate using an SPR angle measurement method in another document (Yuzuru Iwasaki1, 2, 7, Tatsuya Tobita3, Kazuyoshi Kurihara4, Tsutomu Horiuchi I, Koji Suzuki and Osamu Niwa, "MEASUREMENT SCIENCE AND TECHNOLOGY", Meas. Sci. Technol. 17, 2006, p 3184-3188). However, a change of an SPR angle in an area at a different location is not used, and measurement is not performed with a higher precision than that of the present embodiment.

Next, an operation of the antigen concentration measurement apparatus 300a according to the present embodiment will be described with reference to FIGS. 4 and 7.

Figure 7:
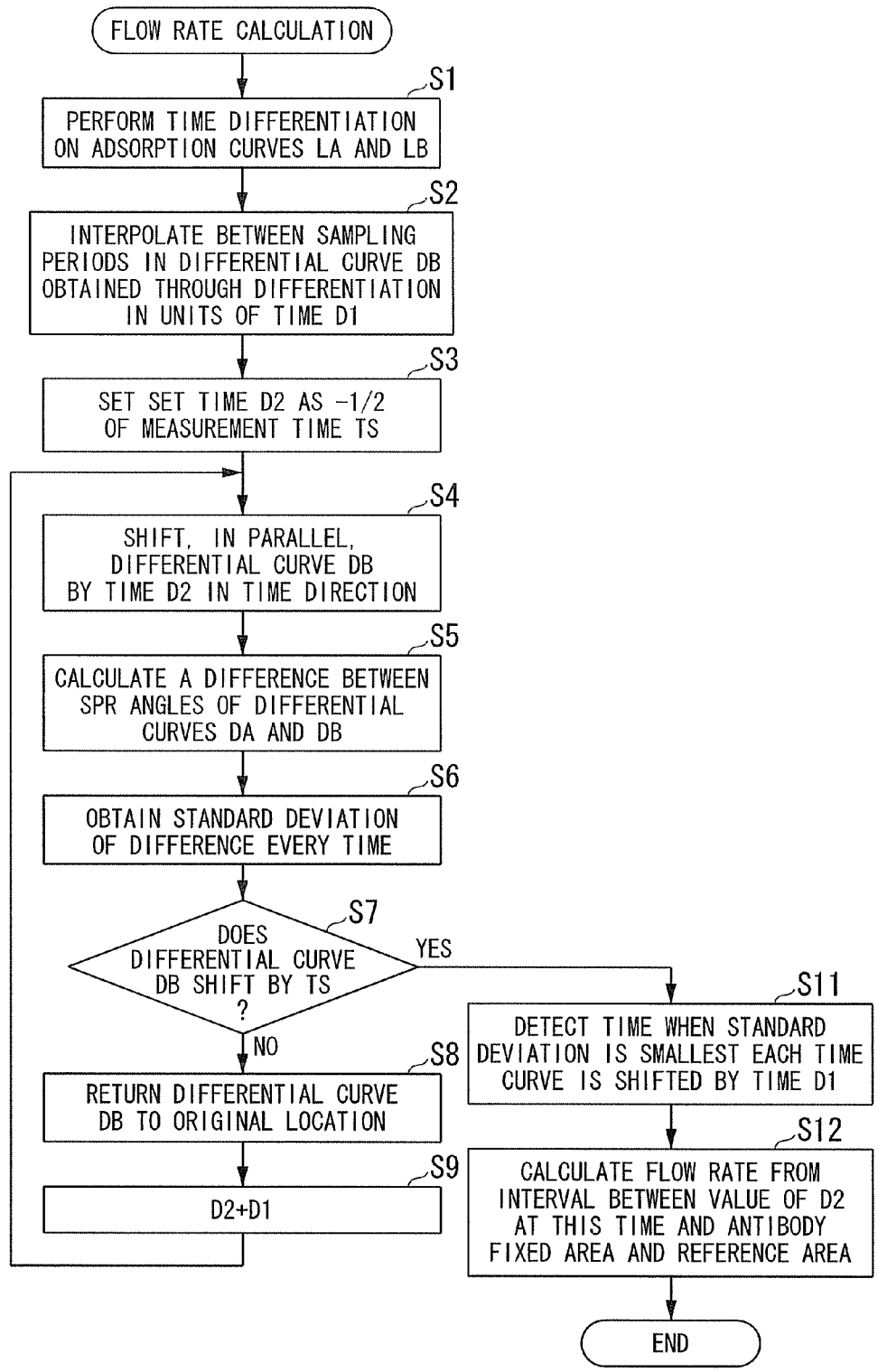
FIG. 7 is a flowchart showing an example of an operation of a process of calculating a flow rate of a sample in the present embodiment.

FIG. 7 is a flowchart showing an example of an operation of a flow rate estimation process in the antigen concentration measurement apparatus 300a of FIG. 4.

In the following description, adsorption curves LA and LB showing a temporal change of an SPR angle in the antibody fixed area 201 and the reference area 202 are calculated, by the SPR angle calculator 13, from gradient data input by the data input unit 11.

The waveform differentiation operation unit 16 performs time differentiation on the each adsorption curves LA and LB to produce differential curves DA and DB (step S1).

Also, the interpolation operation unit 14 performs linear interpolation on data of the SPR angle in the differential curve DB in units of time D1 between the sampling periods (step S2).

The waveform shifter 15 sets the set time D2 as −½ of a measurement time Ts, i.e., −(½)Ts (step S3), and shifts, in parallel, the differential curve DB by the set time D2 in a time direction (step S4).

When the differential curve DB is shifted, the waveform subtractor 17 subtracts an SPR angle at a corresponding time in the differential curve DB from an SPR angle at each time in the differential curve DA to calculate differential data of each time (step S5).

Also, the standard-deviation operation unit 18 obtains the standard deviation of the differential data of each time, and stores the standard deviation together with set-time identification information for identifying the set time D2 at this time, in the data storage unit 12 (step S6).

Next, the waveform shifter 15 determines whether the set time D2 is (½)Ts or not, i.e., whether the range in which the differential curve DB is shifted back and forth from an original location is Ts or not (step S7). When the set time D2 is less than (½)Ts, the process proceeds to step S8, and when the set time D2 is (½)Ts or greater, the process proceeds to step S11.

When the set time D2 is less than (½)Ts, the waveform shifter 15 returns the differential curve DB to a location before shifting the differential curve DB in parallel (step S8) and adds a time D1 to the adsorption-curve set time D2 to obtain a new set time D2 (step S9). The process proceeds to step S4.

Meanwhile, in step S7, when the set time D2 is (½)Ts or greater, the time difference detector 19 sequentially reads a standard deviation every set time D2 corresponding to the set-time identification information from the data storage unit 12 and performs a comparison in a reading order to detect the smallest standard deviation, extract the set-time identification information corresponding to the standard deviation, and output the set time D2 corresponding to the set-time identification information as a time difference between times when the sample reaches the antibody fixed area 201 and the reference area 202 (step S11).

Next, the flow rate calculator 20 divides the distance between locations of two points in the antibody fixed area 201 (e.g., the antibody fixed area 201a of FIG. 2) and the reference area 202 (e.g., the reference area 202B) by the set time D2 corresponding to the smallest standard deviation, and calculates the flow rate of the sample in the flow cell (step S12).

As described above, according to the present embodiment, the flow rate of the sample (liquid or fluid) flowing in the flow cell can be accurately measured, a timing at which the sample reaches the antibody fixed area or the reference area can be detected, an initiation time of the antigen-antibody reaction in the each antibody fixed areas can be corrected with high precision, a reaction rate of the antigen-antibody reaction can be accurately measured, and the antigen concentration can be measured with high precision.

Furthermore, according to the present embodiment, since the timing at which the sample reaches each of the antibody fixed area 201 and the reference area 202 can be accurately detected as described above, common mode noise can be eliminated in the measurement of a difference with the reference area 202, and antigen concentration measurement can be performed with high precision.

Second Embodiment

Next, an antigen concentration measurement apparatus according to a second embodiment of the present invention will be described. Since a configuration of the second embodiment is the same as that of the first embodiment in FIG. 4, a description of the configuration in the second embodiment will be omitted. Hereinafter, operations different from those in the first embodiment will be described.

Pixel data for each light receiving element, i.e., pixel data indicating reflection intensity of the light receiving element corresponding to each location in an arrangement direction of the antibody fixed areas and an incident angle in a previously set incident angle range at each location, is input as arrangement frame image data from the CCD 111 of the SPR sensor in FIG. 1.

The interpolation operation unit 14 performs interpolation, e.g., linear interpolation on the adsorption curve LB in units of time D1. Here, when a sampling period is Ts and the interpolation is performed with a resolution of 1/n, the time D1 is obtained by:

$$D1 = Ts/n.$$

The waveform shifter 15 shifts the adsorption curve LB by a previously set time D2 and then shifts a time range of 2×D2 by the time D1. For example, in the present embodiment, the set time D2 is −(½)Ts and the adsorption curve LB is shifted in parallel by the set time D2, as in the first embodiment.

Further, the waveform shifter 15 adds the time D1 to the set time D2 to obtain a new set time D2, and iteratively shifts the adsorption curve LB in a positive direction from an original location while increasing the set time D2 by the time D1 until the set time D2 is (½)Ts, i.e., the range of the shift time is Ts.

At each time, the waveform subtractor 17 subtracts an SPR angle of the adsorption curve LB from the SPR angle of the adsorption curve LA each corresponding time to obtain SPR differential data of each time, for each value of the set time D2.

The waveform differentiation operation unit 16 performs time differentiation on the difference between the adsorption curve LA and the adsorption curve LB each time to produce differentiated differential data.

The standard-deviation operation unit 18 obtains a standard deviation of the differentiated differential data each time in the measurement range (Ts) of the adsorption curve LA, in units of set time D2, from the result of the time differentiation.

The time difference detector 19 detects a value of the set time D2 having the smallest standard deviation of the differentiated differential data of each time, and the set time D2 is a time difference between times when the sample reaches the antibody fixed area 201 and the reference area 202.

The flow rate calculator 20 obtains a flow rate by dividing a distance between the antibody fixed area 201 and the reference area 202 by the time difference.

Antigen concentration measurement is performed as in the first embodiment described above.

Further, although in the present embodiment, the adsorption curve LA is fixed and the adsorption curve LB is shifted in parallel, conversely, the adsorption curve LB may be fixed and the adsorption curve LA may be shifted to obtain the flow rate similarly.

Next, an operation of the antigen concentration measurement apparatus according to the present embodiment will be described with reference to FIGS. 4 and 8.

Figure 8:
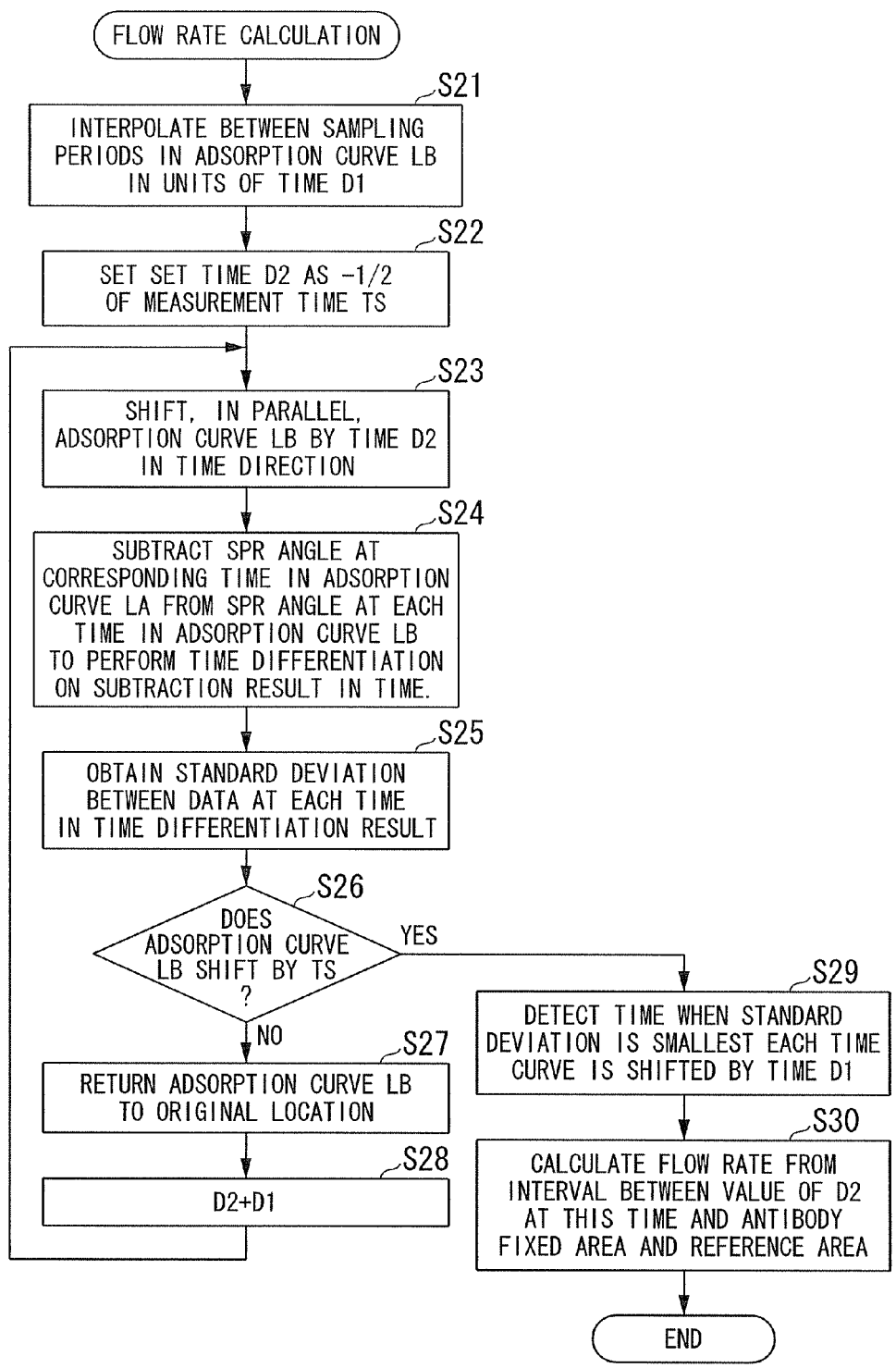
FIG. 8 is a flowchart showing an example of an operation of a process of calculating a flow rate of a sample in a second embodiment of the present invention.

FIG. 8 is a flowchart showing an example of an operation of a flow rate estimation process in the antigen concentration measurement apparatus of FIG. 4.

In the following description, the adsorption curves LA and LB indicating the temporal change of the SPR angle in the antibody fixed area 201 and the reference area 202 are already calculated, by the SPR angle calculator 13, from gradient data input by the data input unit 11.

The interpolation operation unit 14 performs linear interpolation on the data of the SPR angle in the differential curve DB in units of time D1 between sampling periods (step S21).

Next, the waveform shifter 15 sets the set time D2 as −½ of a measurement time Ts, i.e., −(½)Ts, (step S22) and shifts the adsorption curve LB in parallel by the set time D2 in a time direction (step S23).

When the adsorption curve LB is shifted, the waveform subtractor 17 subtracts an SPR angle at a corresponding time in the adsorption curve LB from an SPR angle at each time in the adsorption curve LA to calculate the differential data of each time, and then performs time differentiation on the differential data to generate differentiated differential data (step S24).

After time differentiation is performed on the differential data, the standard-deviation operation unit 18 obtains the standard deviation of the differentiated differential data of each time, and stores the standard deviation together with set-time identification information for identifying the set time D2 at this time in the data storage unit 12 (step S25).

Next, the waveform shifter 15 determines whether the set time D2 is (½)Ts or not, i.e., whether a range in which the differential curve DB is shifted back and forth from an original location is Ts or not (step S26). When the set time D2 is less than (½)Ts, the process proceeds to step S27, and when the set time D2 is (½)Ts or greater, the process proceeds to step S29.

When the set time D2 is less than (½)Ts, the waveform shifter 15 returns the adsorption curve LB to a position before shifting the adsorption curve LB in parallel (step S27), and adds a time D1 to the set time D2 to obtain a new set time D2 (step S28). The process returns to step S23.

Meanwhile, in step S26, when the set time D2 is (½)Ts or greater, the time difference detector 19 sequentially reads the standard deviation at each set time D2 corresponding to the set-time identification information from the data storage unit 12 and performs a comparison in a reading order to detect the smallest standard deviation, extract set-time identification information corresponding to the standard deviation, and output the set time D2 corresponding to the set-time identification information as a time difference between times when the sample reaches the antibody fixed area 201 and the reference area 202 (step S29).

Next, the flow rate calculator 20 divides a distance between locations of two points in the antibody fixed area 201 (e.g., the antibody fixed area 201A of FIG. 2) and the reference area 202 (e.g., the reference area 202B) by the set time D2 corresponding to the smallest standard deviation, and calculates the flow rate of the sample in the flow cell (step S30).

As described above, according to the present embodiment, the flow rate of the sample (liquid or fluid) flowing in the flow cell can be accurately measured, the timing at which the sample reaches the antibody fixed area or the reference area can be detected, an initiation time of an antigen-antibody reaction in each antibody fixed area can be corrected with high precision, the reaction rate of the antigen-antibody reaction can be accurately measured, and the antigen concentration can be measured with high precision, as in the first embodiment.

According to the present embodiment, since the timing at which the sample reaches each of the antibody fixed area 201 and the reference area 202 can be accurately detected as described above, common mode noise can be eliminated in the measurement of the difference with the reference area 202, and antigen concentration measurement can be performed with high precision.

Third Embodiment

Figure 9:
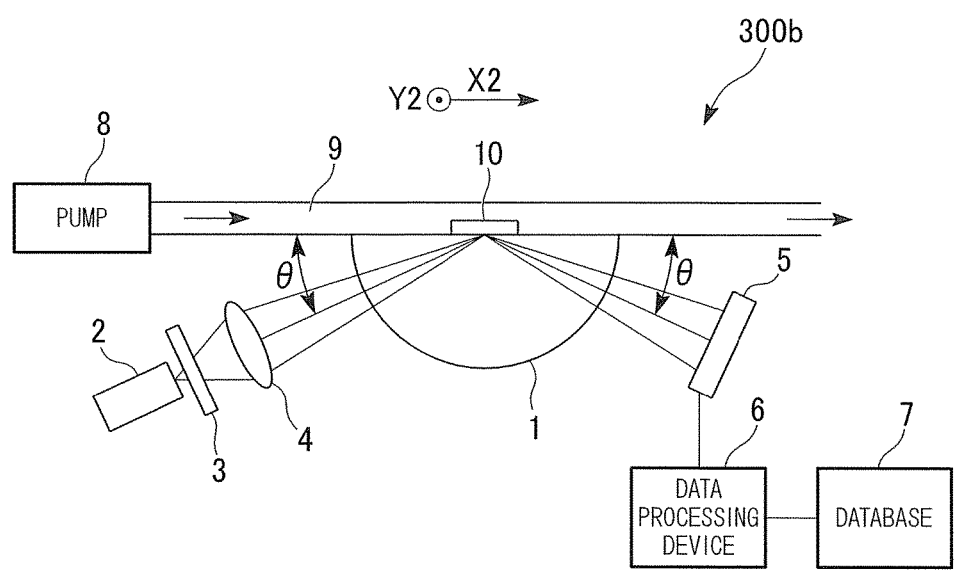
FIG. 9 is a block diagram showing a configuration of an antigen concentration measurement apparatus according to a third embodiment of the present invention.

Next, a third embodiment of the present invention will be described. FIG. 9 is a block diagram showing a configuration of an antigen concentration measurement apparatus 300b according to the third embodiment of the present invention.

The antigen concentration measurement apparatus 300b (referred to also as a flow rate measurement apparatus or an SPR measurement apparatus) of the present embodiment has a prism 1, a light source 2, a polarizer 3, a focusing lens 4, a CCD camera 5, a data processing device 6, a database 7 (referred to also as a storage unit), a pump 8 which transfers a liquid sample to a flow cell 10, and a flow path 9 through which the liquid sample flows.

The prism 1, the light source 2, the polarizer 3, the focusing lens 4, the CCD camera 5, and the data processing device 6 in the antigen concentration measurement apparatus 300b of the present embodiment (FIG. 9) correspond to the prism 104, the LED 100, the polarizer 102, the cylindrical lens 103, the CCD 111, and the data processing device 112 in the antigen concentration measurement apparatus 300a of the first embodiment (FIG. 1), respectively.

Figure 10A:
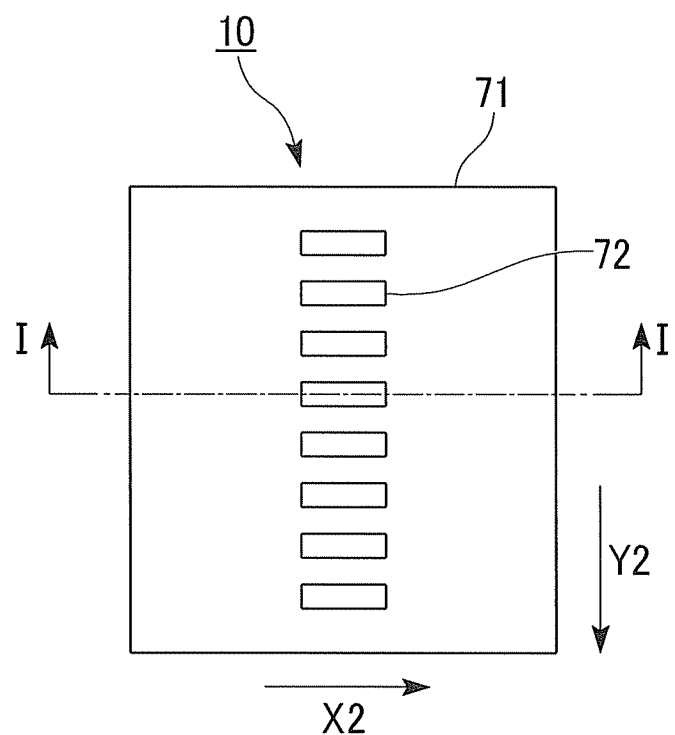
FIG. 10A is a plan view showing a general structure of a sample cell.
Figure 10B:
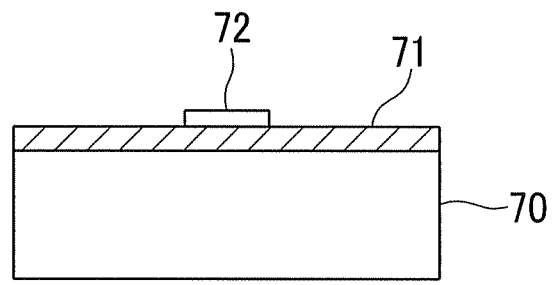
FIG. 10B is a cross-sectional view showing the general structure of the sample cell.

FIG. 10A is a plan view showing a general structure of the flow cell 10, and FIG. 10B is a cross-sectional view taken along a line I-I of the flow cell 10 in FIG. 10A. In FIGS. 10A and 10B, 70 denotes a plate-shaped transparent body formed of a material having the same refractive index as the prism 1, 71 denotes a thin metallic film formed of gold or silver to a thickness of about 40 to 60 nm on the transparent body 70 by sputtering, deposition, and so on, and 72 denotes a measured substance, such as an antibody, fixed on the thin metallic film 71.

Figure 11:
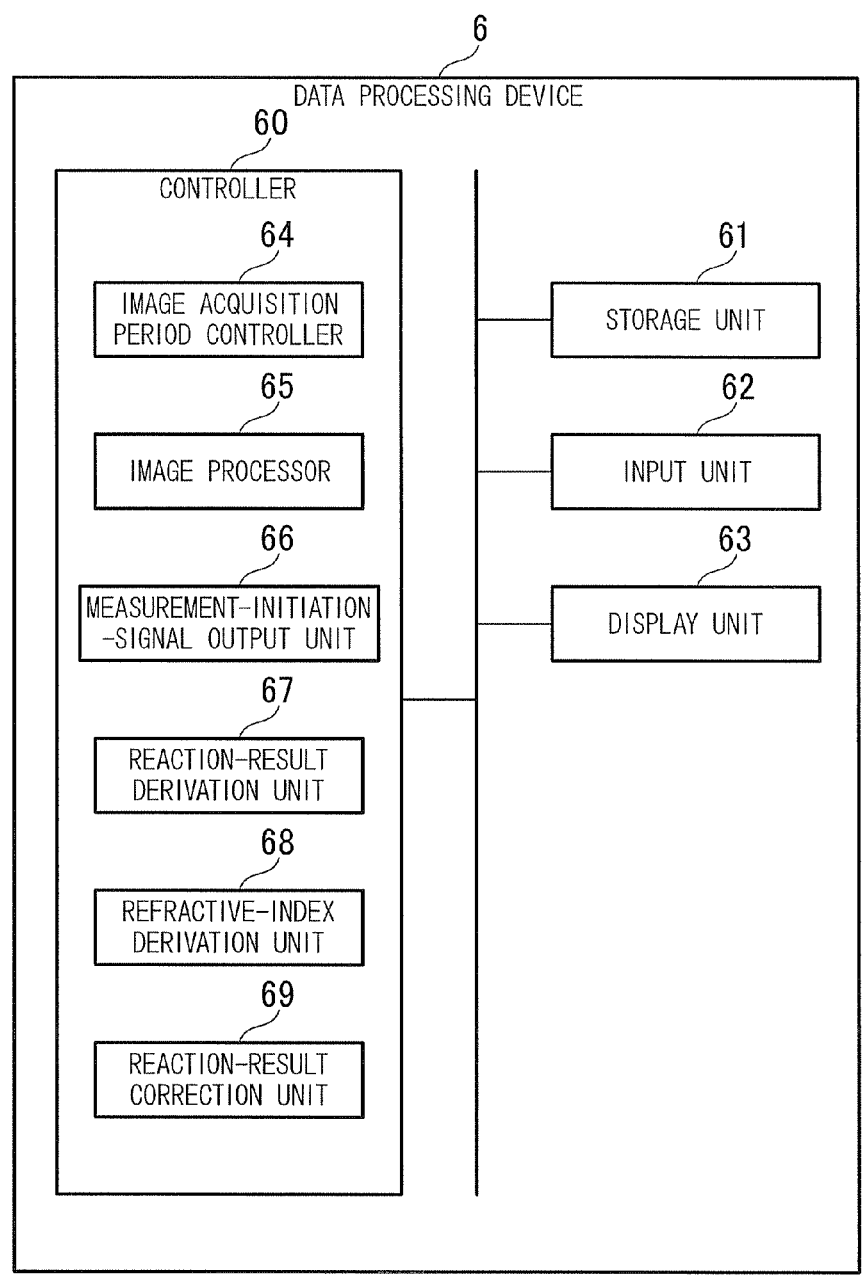
FIG. 11 is a block diagram showing an example of a configuration of a data processing device of an antigen concentration measurement apparatus according to the present embodiment.

FIG. 11 is a block diagram showing an example of a configuration of a data processing device 6. The data processing device 6 has a controller 60 which controls the entire apparatus, a storage unit 61 which stores a program, and so on of the controller 60, an input unit 62 which enables a user of the antigen concentration measurement apparatus 300b to instruct the apparatus, and a display unit 63 which displays information to the user.

The controller 60 has an image acquisition period controller 64, an image processor 65, a measurement-initiation-signal output unit 66, a reaction-result derivation unit 67, a refractive-index derivation unit 68, and a reaction-result correction unit 69.

Figure 12:
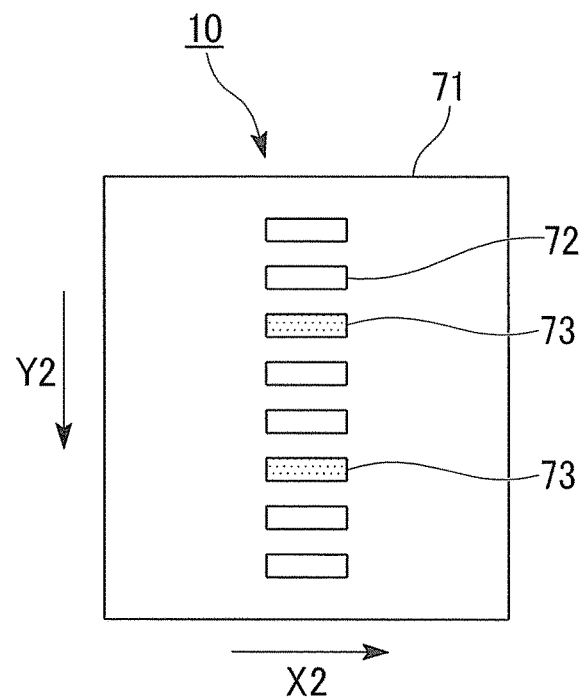
FIG. 12 is a plan view showing a structure of a sample cell used in the present embodiment.

Next, an operation of the antigen concentration measurement apparatus 300b of the present embodiment will be described. FIG. 12 is a plan view showing a structure of the flow cell 10 used in the present embodiment.

In the present embodiment, the flow cell 10 having a thin metallic film 71 formed on a transparent body 70, a measured substance 72 fixed at a measured-substance arrangement place on the thin metallic film 71, and a liquid-sample detection substance 73 (referred to also as a sample detection substance) fixed at a detection substance arrangement place on the thin metallic film 71 is used. The flow cell 10 is disposed on the prism 1 so that the transparent body 70 is contiguous to the prism 1, with the measured substance 72 and the liquid-sample detection substance 73 directed upward.

The liquid-sample detection substance 73 is a substance having a refractive index varying by reacting with a substance other than a substance expected to react with the measured substance 72 among substances contained in the liquid sample. The substance reacting with the liquid-sample detection substance 73 is preferably a high concentration substance in the liquid sample, such as casein when the liquid sample is milk. Examples of the liquid-sample detection substance 73 include anti-casein and anti-BSA when the liquid sample is milk, anti-cow IgG when the milk is colostrum, and an antibody for protein necessarily existing at a high concentration in the milk. Also, other examples of the liquid-sample detection substance 73 include anti-albumin when the liquid sample is blood, and an antibody for protein necessarily existing at a high concentration in the blood.

As in the conventional art, when light from a light source 2 for monochromatic light passes through the polarizer 3, only P-polarized light passes. This P-polarized light is focused by the focusing lens 4, emitted to the prism 1, and emitted to the flow cell 10 from the side of the transparent body 70 opposing the side thereof to which the measured substance 72 is fixed.

Meanwhile, when a liquid sample such as milk is flowed, the pump 8 transfers the liquid sample. Accordingly, the liquid sample flows through the flow path 9 and passes on the flow cell 10.

The image acquisition period controller 64 of the data processing device 6 iteratively outputs an image acquisition timing signal instructing the CCD camera 5 to acquire an image.

When the image acquisition timing signal is output from the data processing device 6, the CCD camera 5 detects reflected light from the flow cell 10 and outputs grayscale image data.

Figure 19:
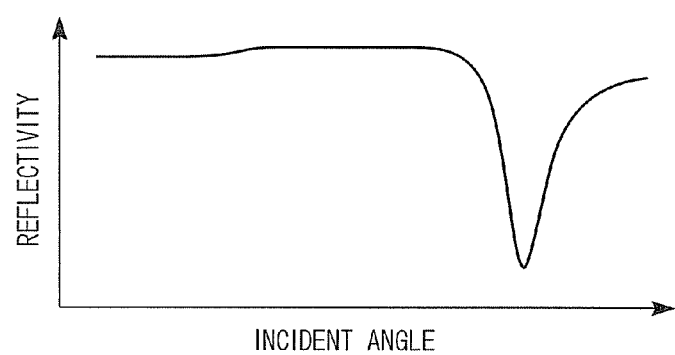
FIG. 19 is a diagram for explaining an example of an incident angle-reflectivity curve obtained by measurement of a sample cell in a conventional antigen concentration measurement apparatus.

The image processor 65 of the data processing device 6 receives the grayscale image data output from the CCD camera 5 and processes the grayscale image data to obtain the data of the incident angle-reflectivity curve as shown in FIG. 19 for each measurement substance 72 and each liquid-sample detection substance 73 of the flow cell 10.

Figure 13:
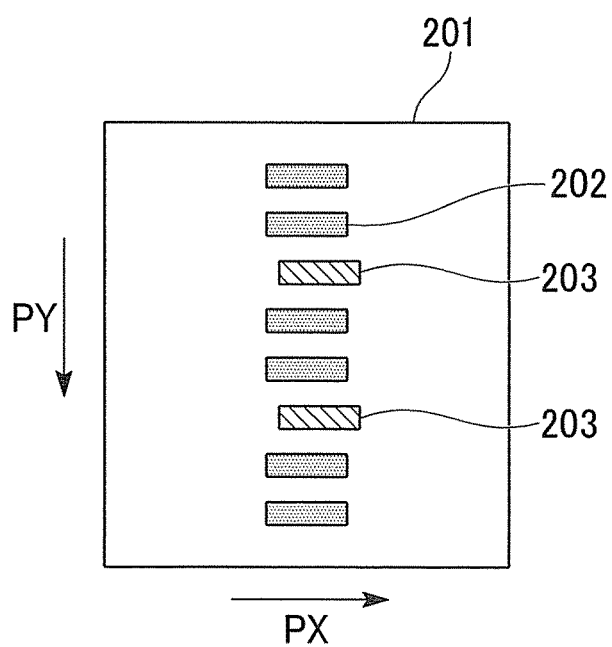
FIG. 13 is a schematic diagram showing an image photographed by a CCD camera in the present embodiment.

FIG. 13 is a schematic diagram showing an image photographed by the CCD camera 5 after the liquid sample is introduced. Grayscale corresponding to reflectivity of the light at each location of the flow cell 10 is shown in the image photographed by the CCD camera 5. In FIG. 13, 201 denotes a bright area (with high reflectivity) corresponding to the thin metallic film 71, 202 denotes a dark area (with low reflectivity) indicating a reflectivity valley caused by the measured substance 72, and 203 denotes a dark area indicating a reflectivity valley caused by the liquid-sample detection substance 73. Deviation of a coordinate of the image area 203 in a PX direction is due to a change in the refractive index due to a reaction between the liquid sample and the liquid-sample detection substance 73 and a slight change in an incident angle at which resonance between the evanescent wave and the surface plasmon wave occurs.

Since the PX direction of FIG. 13 corresponds to the X2 direction of FIG. 9 and indicates an incident angle θ of the light, the image processor 65 can convert the coordinate of the grayscale image data in the PX direction into the incident angle θ. Here, an angle of light to the surface of the thin metallic film 71, which is not perpendicular to the thin metallic film 71, is the incident angle θ. Further, since brightness of the grayscale image in FIG. 13 is changed with the reflectivity of the flow cell 10, the image processor 65 can convert a luminance value for each pixel of the grayscale image data into light reflectivity. In the grayscale image photographed by the CCD camera 5, locations of the measured-substance arrangement place and the detection substance arrangement place of the flow cell 10 are known.

Accordingly, the image processor 65 can obtain the data of the incident angle-reflectivity curve for each measured substance 72 by deriving the incident angle-reflectivity curve on the PY coordinate corresponding to the measured-substance arrangement place for each measured-substance arrangement place. Similarly, the image processor 65 can obtain the data for each liquid-sample detection substance 73 by deriving the incident angle-reflectivity curve on the PY coordinate corresponding to the detection substance arrangement place, for each detection substance arrangement place. The image processor 65 performs this process each time the grayscale image data is output from the CCD camera 5. The PY direction of FIG. 13 corresponds to the Y2 direction perpendicular to a paper surface in FIG. 9.

The measurement in the flow cell 10 by the image acquisition period controller 64, the CCD camera 5, and the image processor 65 is already initiated before the liquid sample is introduced.

Here, the measurement-initiation-signal output unit 66 of the data processing device 6 obtains an incident angle at which the reflectivity is smallest (hereinafter, referred to as resonant angle θsp) from the data of the incident angle-reflectivity curve for the measured substance 72 or the data of the incident angle-reflectivity curve for the liquid-sample detection substance 73 measured by the image processor 65. Also, the measurement-initiation-signal output unit 66 outputs a measurement initiation signal when the resonant angle θsp reaches a value at which the liquid sample may begin to flow on the flow cell 10.

When the measurement initiation signal is output, the image acquisition period controller 64 makes the period of the image acquisition timing signal, i.e., an image acquisition period, shorter than the normal period between an output time of the measurement initiation signal and a predetermined time, and returns the image acquisition period to the normal period after the predetermined time lapses. A reason for changing the image acquisition period will be described below.

Figure 14:
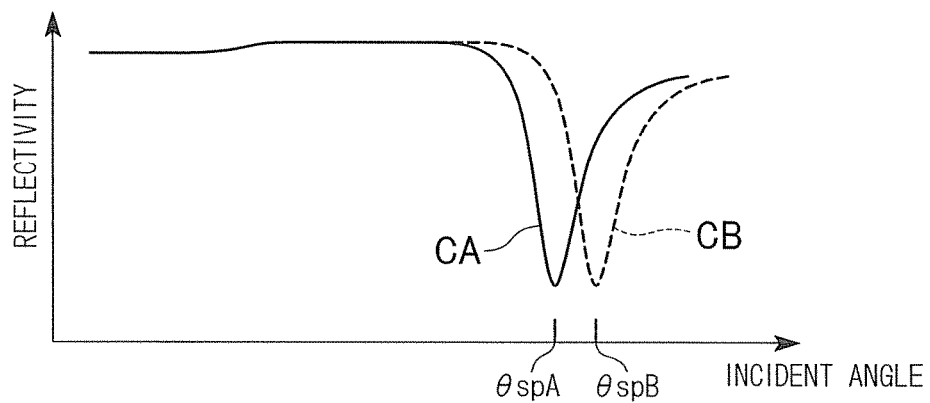
FIG. 14 shows a change of an incident angle-reflectivity curve obtained by measurement of a sample cell after a liquid sample is introduced in the present embodiment.

Next, when the measurement initiation signal is output, the reaction-result derivation unit 67 of the data processing device 6 obtains the resonant angle θsp from the data of the incident angle-reflectivity curve for the measured substance 72 measured by the image processor 65. The resonant angle θsp depends on the refractive index of the measured substance 72 and the refractive index of a substance in the liquid sample that has reacted with the substance 72. When the measured substance 72 (antibody) reacts with the substance in the liquid sample (antigen), the incident angle-reflectivity curve is changed from a property CA to a property CB in FIG. 14 and the resonant angle is changed from θspA to θspB.

A relationship between the change of the resonant angle θsp and a reaction amount between the measured substance 72 and the substance in the liquid sample is registered in the database 7 in advance.

The reaction-result derivation unit 67 can obtain the reaction amount between the measured substance 72 and the substance in the liquid sample from the change of the resonant angle θsp by referring to the database 7. The reaction-result derivation unit 67 performs this process each time the data of the incident angle-reflectivity curve is output from the image processor 65 after the measurement initiation signal is output.

Meanwhile, when the measurement initiation signal is output, the refractive-index derivation unit 68 of the data processing device 6 obtains the resonant angle θsp' from the data of the incident angle-reflectivity curve for the liquid-sample detection substance 73 measured by the image processor 65. The resonant angle θsp' depends on the refractive index of the liquid-sample detection substance 73 and the refractive index of the substance in the liquid sample that has reacted with the liquid-sample detection substance 73.

A relationship between the resonant angle θsp' and the refractive index is registered in the database 7 in advance.

The refractive-index derivation unit 68 can obtain the refractive indices of the liquid-sample detection substance 73 and the reacting substance in the liquid sample from the resonant angle θsp' by referring to the database 7.

The refractive-index derivation unit 68 performs this process each time the data of the incident angle-reflectivity curve is output from the image processor 65 after the measurement initiation signal is output.

Figure 15:
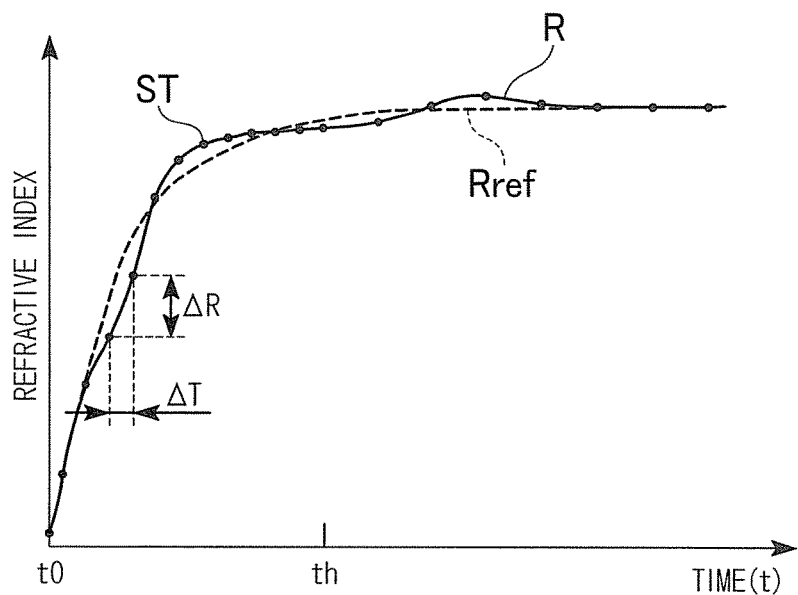
FIG. 15 is a diagram showing a temporal change of a refractive index obtained by a refractive-index derivation unit 68 in the present embodiment.

FIG. 15 is a diagram showing a temporal change of the refractive index obtained by the refractive-index derivation unit 68. In FIG. 15, R indicated by a solid line denotes an actual refractive index obtained by the refractive-index derivation unit 68, Rref indicated by a dotted line denotes an ideal refractive index when the flow rate of the liquid sample is constant, and ST indicated by a circle mark denotes image acquisition timing.

The substance expected to react with the liquid-sample detection substance 73 is a substance existing at a high concentration in the liquid sample. Accordingly, reaction between the substance and the liquid-sample detection substance 73 suddenly occurs after the liquid sample is introduced, and the refractive index R obtained at each image acquisition time by the refractive-index derivation unit 68 is suddenly increased and then saturated as shown in FIG. 15. However, this refractive index R deviates from the ideal refractive index Rref due to variation in the flow rate of the liquid sample.

Here, when the image acquisition period is ΔT and the change amount of the refractive index R in the period ΔT is ΔR, the rate of change of the refractive index R, V=ΔR/ΔT, is in proportion to the flow rate of the liquid sample.

Accordingly, an amount of error of the rate of change V can be obtained by comparing a known rate of change Vref of the refractive index when the flow rate of the liquid sample has an ideal value with the rate of change V of an actual refractive index R, and an amount of error between the actual flow rate and the ideal flow rate of the liquid sample can be obtained from the amount of error of the rate of change V. Since the result of the reaction between the measured substance 72 and the substance in the liquid sample depends on the flow rate (flow quantity) of the liquid sample, when the amount of error of the flow rate can be obtained, it is possible to know how much the reaction result is to be corrected.

The ideal value Vref of the rate of change of the refractive index R is registered in the database 7 in advance, every elapsed time t from the measurement initiation time t0. The amount of error between the rate of change V and the ideal value Vref and the amount of error of the flow rate are also registered to correspond to each other in the database 7 in advance. The amount of error of the flow rate and a correction amount of the reaction amount are also registered to correspond to each other in the database 7 in advance.

The reaction-result correction unit 69 calculates a change amount ΔR from a current refractive index R and a refractive index R before one period at a time t after the time t0 at which the measurement initiation signal is output, to calculate the rate of change of the refractive index R, V=ΔR/ΔT, and acquires the ideal value Vref of the rate of change at the current time t by referring to the database 7 to calculate the amount of error of the rate of change V. Also, the reaction-result correction unit 69 acquires an amount of error of the flow rate corresponding to the amount of error of the rate of change V from the database 7, and acquires the correction amount corresponding to the amount of error of the flow rate from the database 7 to correct the reaction amount obtained by the reaction-result derivation unit 67 according to the correction amount. The reaction-result correction unit 69 performs this process each time data of the refractive index R is output from the refractive-index derivation unit 68 after the measurement initiation signal is output.

By doing so, in the present embodiment, it is possible to correct the reaction result of the measured substance 72 even when the flow rate of the liquid sample is changed.

As apparent from the above description, the CCD camera 5, the image processor 65, the reaction-result derivation unit 67, the refractive-index derivation unit 68 and the reaction-result correction unit 69 operate at each image acquisition period. Since the refractive index obtained by the refractive-index derivation unit 68 is suddenly increased and saturated as shown in FIG. 15, it is preferable to increase the correction precision by making the measurement period shorter in an elevation period. This is the reason that the image acquisition period controller 64 changes the image acquisition period. That is, the image acquisition period controller 64 makes the period of the image acquisition timing signal shorter than the normal period between the time t0 at which the measurement initiation signal is output and a predetermined time th, and returns the period of the image acquisition timing signal to the normal period after the time th lapses.

The antigen concentration measurement apparatus according to a conventional technique transfers a liquid sample such as milk to a pump and flows the liquid sample on a sample cell to detect a reaction between, for example, bacteria contained in the milk and an antibody fixed to a sample cell. However, in the antigen concentration measurement apparatus according to a conventional technique, when a flow rate of the liquid sample is changed, it is impossible to correct the result of the reaction. For example, in the case of a simple apparatus incapable of adjusting the flow rate of the liquid sample with high precision or when the flow rate is smaller than a value expected in a liquid transfer mechanism due to a viscosity difference in the liquid sample, a reaction amount between the antigen and the antibody decreases, and when the flow rate is greater than the ideal value, the reaction amount between the antigen and the antibody increases. Thus, when the flow rate of the liquid sample is changed, correct measurement cannot be performed.

However, according to the present embodiment, the flow cell 10 in which the liquid-sample detection substance 73 having a refractive index varying by reacting with a substance other than a substance expected to react with the measured substance among substances contained in the liquid sample is fixed to the thin metallic film is irradiated with light at a state in which the liquid sample flows, to obtain the resonant angle, which is an incident angle at which the reflectivity of light is smallest, from the incident angle-reflectivity curve for the liquid-sample detection substance 73 obtained from the image photographed by the CCD camera 5, obtain the refractive indices of the liquid-sample detection substance 73 and the reacting substance in the liquid sample from the resonant angle, obtain the amount of error of the flow rate of the liquid sample from the rate of change of the refractive index, and obtain the correction amount for the reaction amount from the amount of error of the flow rate, such that the reaction amount obtained by the reaction-result derivation unit 67 can be corrected. As a result, according to the present embodiment, it is possible to correct the measurement result according to the change of the flow rate of the liquid sample.

In the present embodiment, when the resonant angle is obtained from the incident angle-reflectivity curve obtained by the image processor 65 and the liquid sample beginning to flow on the flow cell 10 is detected from the change of the resonant angle, the measurement initiation signal is output and the period of the image acquisition timing signal is made shorter than the normal period between an output time of the measurement initiation signal and a predetermined time, thereby achieving high correction precision for the measurement result.

Fourth Embodiment

Next, a fourth embodiment of the present invention will be described. A description of the same portions of the present invention as in the first embodiment will be omitted. The fourth embodiment differs from the first embodiment in a method of obtaining the flow rate of the sample flowing in the flow cell. Accordingly, the differences will now be described.

Figure 16:
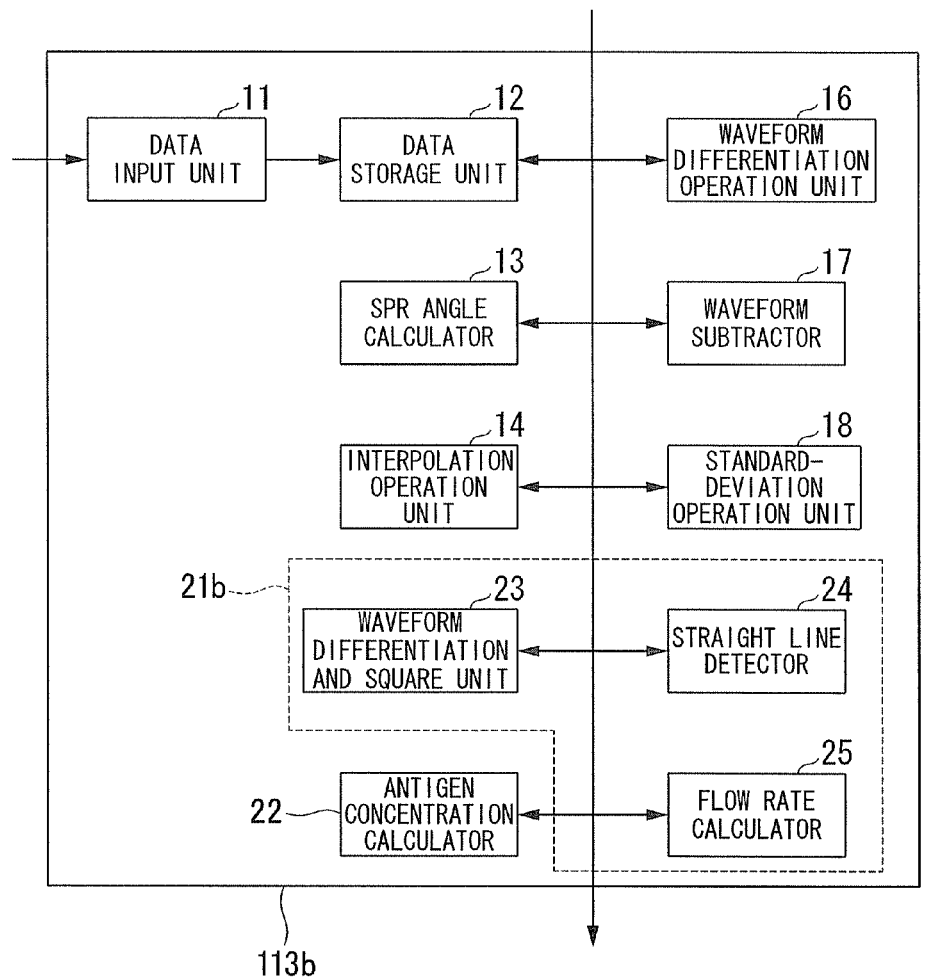
FIG. 16 is a block diagram showing a configuration of a controller 113b of a data processing device of an antigen concentration detecting apparatus according to a fourth embodiment of the present invention.

FIG. 16 is a block diagram showing a configuration of a controller 113b of a data processing device in an antigen concentration detecting apparatus according to a fourth embodiment of the present invention.

The controller 113b has a data input unit 11, a data storage unit 12, an SPR angle calculator 13, an interpolation operation unit 14, a waveform differentiation operation unit 16, a waveform subtractor 17, a standard-deviation operation unit 18, a waveform differentiation and square unit 23, a straight line detector 24, and a flow rate detector 25.

The fourth embodiment of the present invention differs from the first embodiment in which the controller 113a has the waveform shifter 15, the time difference detector 19, and the flow rate calculator 20, in that the controller 113b has the waveform differentiation and square unit 23, the straight line detector 24, and the flow rate detector 25.

Further, the waveform differentiation and square unit 23, the straight line detector 24, and the flow rate detector 25 are collectively termed as a flow rate operation unit 21b.

First, the antigen concentration detecting apparatus of the present embodiment flows a sample having a low refractive index through a flow path of a flow cell in a Y1 direction (see FIGS. 1 and 2). Here, the refractive index of this sample is N1.

Next, the antigen concentration detecting apparatus of the present embodiment flows a sample having a high refractive index through the flow path of the flow cell in the Y1 direction. Here, the refractive index of this sample is N2. There is a relationship of N2>N1 between the refractive index N1 and the refractive index N2.

Next, the antigen concentration detecting apparatus of the present embodiment flows the sample having a low refractive index through the flow path of the flow cell in the Y1 direction. This sample refractive index is N1.

When this process is performed, a temporal change of the refractive index at a plurality of points in the Y1 direction of the flow cell is measured such that an arrangement indicating a refractive index at each time and at each point can be obtained. A graph as shown in FIG. 17(a) is obtained by indicating the arrangement using a contour line.

Figure 17:
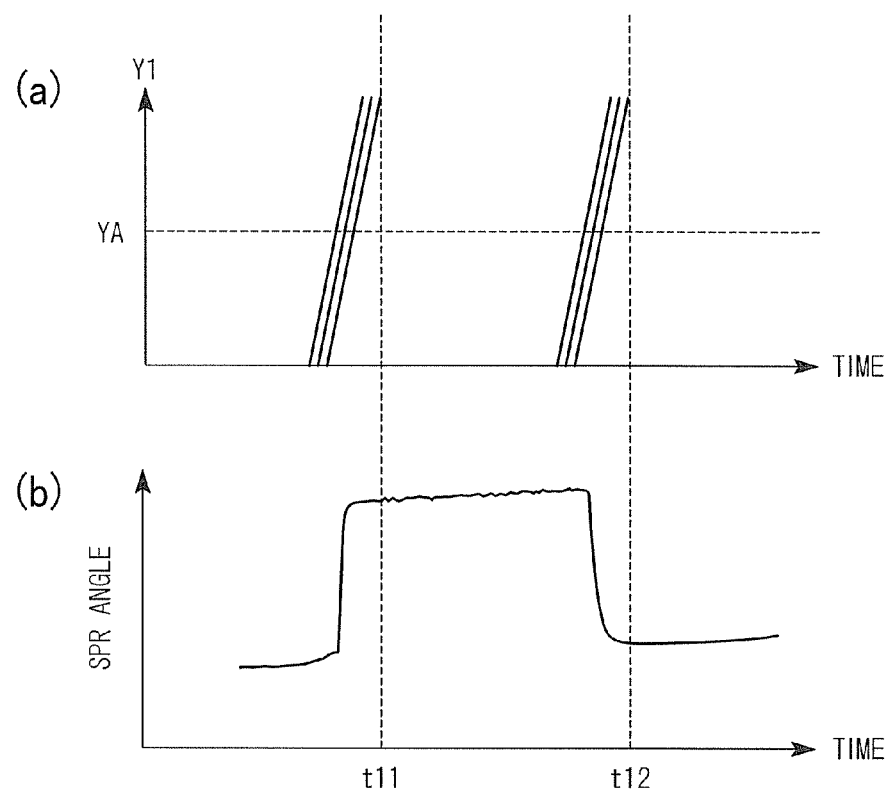
FIG. 17 is a diagram for explaining a method of obtaining a flow rate in the present embodiment.
Figure 18:
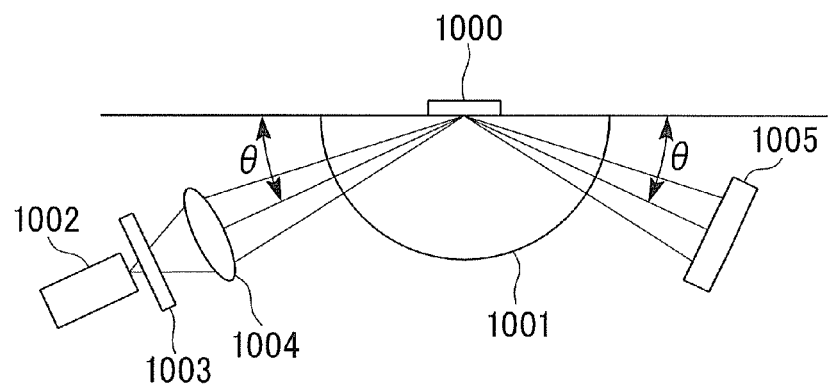
FIG. 18 is a schematic block diagram showing a configuration of a conventional antigen concentration measurement apparatus.

In FIG. 17(a), a horizontal axis denotes a time and a vertical axis denotes a distance from a predetermined point of the flow path of the flow cell.

In FIG. 17(a), three straight lines having a positive slope are plotted around a time t11. In FIG. 17(b), three straight lines having a positive slope are also plotted around a time t12. Points connected by the each straight lines mean that the SPR angles are the same.

Where a flow rate of a sample flowing in the flow cell is very high, slopes of the three straight lines around the time t11 and the three straight lines around the time t12 become closer to a slope of the vertical axis (Y1 axis) in FIG. 17(a). That is, the slope of each straight line approaches infinity.

Where the flow rate of the sample flowing in the flow cell is low, the slopes of the three straight lines around the time t11 and the three straight lines around the time t12 are closer to a slope of the horizontal axis (time axis) in FIG. 17(a). That is, the slope of each straight line approaches 0.

When the graph in FIG. 17(a) is observed from a predetermined point (at which Y1=YA) of the flow cell, a graph as shown in FIG. 17(b) is obtained. In FIG. 17(b), a horizontal axis denotes a time and a vertical axis denotes an SPR angle.

The straight line detector 24 of the controller 113b of FIG. 16 detects a straight line portion from an image of FIG. 17(a). The straight line detector 24 of the present embodiment detects the straight line portion from the image of FIG. 17(a) using Hough conversion, which is a known image processing algorithm. Alternatively, the straight line detector 24 may detect the straight line portion from the image using a known image process algorithm other than the Hough conversion.

The waveform differentiation and square unit 23 differentiates the arrangement data of FIG. 17(a) in a time direction so that the straight line detector 24 using the Hough conversion is suitable for detecting a portion in which the flow rate is changed. Thereafter, the waveform differentiation and square unit 23 performs a square process.

The flow rate detector 25 obtains the slope of the straight line from the operation result of the straight line detector 24 to calculate the flow rate of the sample flowing in the flow cell.

In the first embodiment, it is necessary to determine two points of the antibody fixed area 201 or the reference area 202 in advance, and it is possible to obtain the flow rate in a specific section of the flow cell. In the fourth embodiment, since the flow rate can be obtained from the slope of the straight line, a temporal change of the flow rate can be obtained depending on a location in the flow cell. Accordingly, high processing precision in the antigen concentration detecting apparatus can be achieved.

Further, although the case in which Hough conversion is used to obtain the flow rate has been described in the fourth embodiment, this method may be applied to the second or third embodiment.

A program for realizing functions of the each parts (FIGS. 4, 11 and 16) of the data processing device in the antigen concentration measurement apparatus according to the first to fourth embodiments may be recorded in a computer-readable recording medium and read by a computer system to perform the process of detecting the flow rate of the sample. Further, the "computer system" herein includes an operating system (OS) and hardware such as peripheral devices. The "computer system" also includes a WWW system having a homepage providing environment (or a display environment). The "computer-readable recording medium" includes a storage device such as a flexible disk, a magnetic optical disk, a ROM, a portable medium such as CD-ROM, and a hard disk included in a computer system. Also, the "computer-readable recording medium" includes a medium that stores a program for a predetermined time, like a volatile memory (RAM) in a computer system consisting of a server and a client when a program is transmitted via a network such as the Internet or a communication line such as telephone line.

Further, the program may be transmitted from a computer system in which the program is stored in a storage device, and so on to other computer systems via a transmission medium or by a transmission wave in the transmission medium. Here, the "transmission medium" for transmitting the program refers to a medium having a function of transmitting information, such as a network (communication network) such as the Internet or a communication line such as a telephone line. Also, the program may be a program for realizing a portion of the above-described function. Alternatively, the program may be a program capable of realizing the above-described function through a combination with a program previously stored in a computer system, i.e., a differential file (differential program).

INDUSTRIAL APPLICABILITY

The present invention is applicable to a flow rate measurement apparatus, an antigen concentration measurement apparatus, a flow cell, a flow rate measurement method, an antigen concentration measurement method, and so on capable of accurately measuring the flow rate of the sample in the flow cell and detecting an antibody area that the sample reaches in the area to which a plurality of serially arranged antibodies are fixed.

The invention claimed is:

1. A flow rate measurement method of measuring a flow rate of a sample flowing in a long flow cell using a flow rate measurement apparatus comprising: a light oscillator, a thin metallic film which causes surface plasmon resonance by light output from the light oscillator; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and the reference areas being alternately arranged in the flow cell and the flow cell being formed at a location along the focal line location on the thin metallic film; and a light receiver which receives reflected light, at the focal line location, of the output light by surface plasmon resonance occurring at the focal line location, at each of the plurality of incident light angles, the flow rate measurement method comprising:
an SPR angle calculation process of obtaining temporal change of each of SPR angles in each of the antibody fixed areas and the reference areas in the measurement part; and
a flow rate operation process of calculating the flow rate of the sample flowing in the flow cell based on the temporal change of each of the SPR angles obtained by the SPR angle calculation process.

2. The flow rate measurement method according to claim 1, wherein the flow rate operation process comprises:
a waveform shift process of shifting one of adsorption curves indicating the temporal change of the SPR angles at two points, where one point is in the antibody fixed area and the other point is in the reference area, with respect to the other in a time direction;
a time difference detection process of measuring a shift time at which a difference between the SPR angles at the two points is smallest; and
a flow rate calculation process of calculating the flow rate of the sample in the flow cell by dividing a location between the two points by the shift time.

3. The flow rate measurement method according to claim 2, further comprising a waveform differentiation operation process of performing time differentiation on the adsorption curves for the two each points to obtain differential curves,
wherein one of the differential curves for the two each points with respect to the other in a time direction is shifted in the waveform shift process, and a shift time at which a difference between the SPR angles in the differential curves for the two each points is smallest is measured in the time difference detection process.

4. The flow rate measurement method according to claim 2, further comprising a waveform differentiation operation process of performing time differentiation on differential data of the SPR angles,
wherein one of the adsorption curves for the two each points with respect to each other in a time direction is shifted in the waveform shift process, and
the adsorption curve is shifted each time in the waveform shift process, the time differentiation on differential data of the adsorption curves for the two each points is performed in the waveform differentiation operation process, and a shift time at which the time-differentiated differential data of SPR angles in the adsorption curves for the two each points is smallest is measured in the time difference detection process.

5. The flow rate measurement method according to claim 1, wherein the flow rate of the sample flowing in the flow cell using Hough conversion is calculated in the flow rate operation process.

6. The flow rate measurement method according to claim 1, wherein the antibody, and a sample detection substance having a refractive index varying by reacting with a substance other than a substance expected to react with the antibody among substances contained in the sample are fixed on the thin metallic film, and the flow rate measurement method further comprises:
a reaction-result derivation process of obtaining a resonant angle that is an incident angle at which reflectivity is smallest based on a correlation between the incident angle of the incident light and reflectivity of the reflected light in the antibody, and obtaining a reaction amount between the antibody and the sample detection substance from the resonant angle;
a refractive-index derivation process of obtaining a resonant angle based on a correlation between the incident angle and reflectivity in the sample detection substance, and obtaining refractive indices of the sample detection substance and the substance contained in the reacting sample from the resonant angle; and
a reaction-result correction process of obtaining an amount of error for the flow rate of the sample from a rate of change of the refractive index obtained by the refractive-index derivation process and obtaining a correction amount for the reaction amount obtained by the reaction-result derivation process from an amount of error of the flow rate to correct the reaction amount based on the correction amount.

7. The flow rate measurement method according to claim 6, further comprising:
a measurement-initiation-signal output process of outputting a measurement initiation signal in case that the resonant angle is obtained from the correlation between then incident angle and the reflectivity obtained by an image processor and the sample beginning to flow on the flow cell is detected from a change of the resonant angle; and
an image acquisition period control process of iteratively outputting an image acquisition timing signal to instruct the light receiver to acquire an image, making the period of the image acquisition timing signal shorter than the normal period between an output time of the measurement initiation signal and a predetermined time, and returning the period of the image acquisition timing signal to the normal period after the predetermined time lapses.

8. The flow rate measurement method according to claim 6, further comprising a storage process of registering, in advance, the ideal value of the rate of change of the refractive index, a relationship between the amount of error of the rate of change and the amount of error for the flow rate of the sample, and a relationship between the amount of error of the flow rate and the correction amount are registered in advance,
wherein an amount of error between the rate of change of the refractive index obtained by the refractive-index derivation process and the ideal value of the rate of change registered by the storage process are obtained in the reaction-result correction process, the amount of error of the flow rate corresponding to the amount of error of the rate of change stored by the storage process is acquired, and the correction amount corresponding to the amount of error of the flow rate stored by the storage process is acquired.

9. The flow rate measurement method according to claim 1, wherein the flow rate operation process comprises:
a waveform differentiation and square process of differentiating, in a time direction, an arrangement data indicating a refractive index at each time and at each point, and performing a square process;
a straight line detection process of detecting a straight line portion, based on the result by the waveform differentiation and square process, by using an image processing algorithm; and
a flow rate detection process of obtaining, based on the result by the straight line detection process, a slope of a straight line, and calculating the flow rate of the sample flowing in the flow cell.

10. The flow rate measurement method according to claim 1,
wherein the flow rate of the sample flowing in the flow cell using Hough conversion is calculated in the flow rate operation process, and
wherein the antibody, and a sample detection substance having a refractive index varying by reacting with a substance other than a substance expected to react with the antibody among substances contained in the sample are fixed on the thin metallic film, and the flow rate measurement method further comprises:
a reaction-result derivation process of obtaining a resonant angle that is an incident angle at which reflectivity is smallest based on a correlation between the incident angle of the incident light and reflectivity of the reflected light in the antibody, and obtaining a reaction amount between the antibody and the sample detection substance from the resonant angle;
a refractive-index derivation process of obtaining a resonant angle based on a correlation between the incident angle and reflectivity in the sample detection substance, and obtaining refractive indices of the sample detection substance and the substance contained in the reacting sample from the resonant angle; and
a reaction-result correction process of obtaining an amount of error for the flow rate of the sample from a rate of change of the refractive index obtained by the refractive-index derivation process and obtaining a correction amount for the reaction amount obtained by the reaction-result derivation process from an amount of error of the flow rate to correct the reaction amount based on the correction amount.

11. An antigen concentration measurement method of measuring a flow rate of a sample flowing in a long flow cell using a flow rate measurement apparatus comprising: a light oscillator; a thin metallic film which causes surface plasmon resonance by light output from the light oscillator, the antibody and a sample detection substance having a refractive index varying by reacting with a substance other than an antigen expected to react with the antibody among substances contained in the sample being fixed on the thin metallic film; a focusing unit which fixes the thin metallic film and converts the output light of the light oscillator into incident light having a plurality of incident angles to focus the incident light at a location of a focal line in a straight line shape on the thin metallic film; a measurement part having antibody fixed areas to which an antibody is fixed and reference areas to which an antibody is not fixed, the antibody fixed areas and the reference areas being alternately arranged in the flow cell and the flow cell being formed at a location along the focal line location on the thin metallic film; and a light receiver which receives reflected light, at the focal line location, of the output light by surface plasmon resonance occurring at the focal line location, at each of the plurality of incident light angles, an antigen concentration measurement method comprising:
an SPR angle calculation process of obtaining a temporal change of each of SPR angles in each of the antibody fixed areas and the reference areas in the measurement part;
a flow rate operation process of calculating a flow rate of the sample flowing in the flow cell based on the temporal change of each of the SPR angles obtained in the SPR angle calculation process;
a reaction-result derivation process of obtaining a resonant angle that is an incident angle at which reflectivity is smallest based on a correlation between the incident angle of the incident light and reflectivity of the reflected light in the antibody, and obtaining a reaction amount between the antibody and the sample detection substance from the resonant angle;
a refractive-index derivation process of obtaining a resonant angle based on a correlation between the incident angle and reflectivity in the sample detection substance, and obtaining refractive indices of the sample detection substance and the substance contained in the reacting sample from the resonant angle;
a reaction-result correction process of obtaining an amount of error for the flow rate of the sample from a rate of change of the refractive index obtained in the refractive-index derivation process and obtaining a correction amount for the reaction amount obtained in the reaction-result derivation process from an amount of error of the flow rate to correct the reaction amount based on the correction amount; and an antigen concentration calculation process of calculating a concentration of the antigen contained in the sample based on the correction result in the reaction result correction process.

12. The antigen concentration measurement method according to claim 11, wherein the flow rate operation process comprises:
   a waveform shift process of shifting one of adsorption curves indicating the temporal change of the SPR angles at two points, where one point is in the antibody fixed area and the other point is in the reference area, with respect to the other in a time direction;
   a time difference detection process of measuring a shift time at which a difference between the SPR angles at the two points is smallest; and
   a flow rate calculation process of calculating the flow rate of the sample in the flow cell by dividing a location between the two points by the shift time.

13. The antigen concentration measurement method according to claim 12, further comprising a waveform differentiation operation process of performing time differentiation on the adsorption curves for the two each points to obtain differential curves,
   wherein one of the differential curves for the two each points with respect to the other in a time direction is shifted in the waveform shift process, and a shift time at which a difference between the SPR angles in the differential curves for the two each points is smallest is measured in the time difference detection process.

14. The antigen concentration measurement method according to claim 12, further comprising a waveform differentiation operation process of performing time differentiation on differential data of the SPR angles,
   wherein one of the adsorption curves for the two each points with respect to each other in a time direction is shifted in the waveform shift process, and
   the adsorption curve is shifted each time in the waveform shift process, the time differentiation on differential data of the adsorption curves for the two each points is performed in the waveform differentiation operation process, and a shift time at which the time-differentiated differential data of SPR angles in the adsorption curves for the two each points is smallest is measured in the time difference detection process.

15. The antigen concentration measurement method according to claim 11, wherein the flow rate of the sample flowing in the flow cell using Hough conversion is calculated in the flow rate operation process.

16. The antigen concentration measurement method according to claim 11, wherein the antibody, and a sample detection substance having a refractive index varying by reacting with a substance other than a substance expected to react with the antibody among substances contained in the sample are fixed on the thin metallic film, and the antigen concentration measurement method further comprises:
   a reaction-result derivation process of obtaining a resonant angle that is an incident angle at which reflectivity is smallest based on a correlation between the incident angle of the incident light and reflectivity of the reflected light in the antibody, and obtaining a reaction amount between the antibody and the sample detection substance from the resonant angle;
   a refractive-index derivation process of obtaining a resonant angle based on a correlation between the incident angle and reflectivity in the sample detection substance, and obtaining refractive indices of the sample detection substance and the substance contained in the reacting sample from the resonant angle; and
   a reaction-result correction process of obtaining an amount of error for the flow rate of the sample from a rate of change of the refractive index obtained by the refractive-index derivation process and obtaining a correction amount for the reaction amount obtained by the reaction-result derivation process from an amount of error of the flow rate to correct the reaction amount based on the correction amount.

17. The antigen concentration measurement method according to claim 16, further comprising:
   a measurement-initiation-signal output process of outputting a measurement initiation signal in case that the resonant angle is obtained from the correlation between then incident angle and the reflectivity obtained by an image processor and the sample beginning to flow on the flow cell is detected from a change of the resonant angle; and
   an image acquisition period control process of iteratively outputting an image acquisition timing signal to instruct the light receiver to acquire an image, making the period of the image acquisition timing signal shorter than the normal period between an output time of the measurement initiation signal and a predetermined time, and returning the period of the image acquisition timing signal to the normal period after the predetermined time lapses.

18. The antigen concentration measurement method according to claim 16, further comprising a storage process of registering, in advance, the ideal value of the rate of change of the refractive index, a relationship between the amount of error of the rate of change and the amount of error for the flow rate of the sample, and a relationship between the amount of error of the flow rate and the correction amount are registered in advance,
   wherein an amount of error between the rate of change of the refractive index obtained by the refractive-index derivation process and the ideal value of the rate of change registered by the storage process are obtained in the reaction-result correction process, the amount of error of the flow rate corresponding to the amount of error of the rate of change stored by the storage process is acquired, and the correction amount corresponding to the amount of error of the flow rate stored by the storage process is acquired.

19. The antigen concentration measurement method according to claim 11, wherein the flow rate operation process comprises:
   a waveform differentiation and square process of differentiating, in a time direction, an arrangement data indicating a refractive index at each time and at each point, and performing a square process;
   a straight line detection process of detecting a straight line portion, based on the result by the waveform differentiation and square process, by using an image processing algorithm; and
   a flow rate detection process of obtaining, based on the result by the straight line detection process, a slope of a straight line, and calculating the flow rate of the sample flowing in the flow cell.

20. The antigen concentration measurement method according to claim 11, wherein the flow rate of the sample flowing in the flow cell using Hough conversion is calculated in the flow rate operation process, and wherein the antibody, and a sample detection substance having a refractive index varying by reacting with a substance other than a substance expected to react with the antibody among substances contained in the sample are fixed on the thin metallic film, and the antigen concentration measurement method further comprises:

a reaction-result derivation process of obtaining a resonant angle that is an incident angle at which reflectivity is smallest based on a correlation between the incident angle of the incident light and reflectivity of the reflected light in the antibody, and obtaining a reaction amount between the antibody and the sample detection substance from the resonant angle;

a refractive-index derivation process of obtaining a resonant angle based on a correlation between the incident angle and reflectivity in the sample detection substance, and obtaining refractive indices of the sample detection substance and the substance contained in the reacting sample from the resonant angle; and a reaction-result correction process of obtaining an amount of error for the flow rate of the sample from a rate of change of the refractive index obtained by the refractive-index derivation process and obtaining a correction amount for the reaction amount obtained by the reaction-result derivation process from an amount of error of the flow rate to correct the reaction amount based on the correction amount.

* * * * *